US011517530B2

(12) United States Patent
Wang et al.

(10) Patent No.: US 11,517,530 B2
(45) Date of Patent: Dec. 6, 2022

(54) THERAPEUTIC AGENTS SPECIFICALLY DELIVERED BY EXOSOMES FOR CANCER TREATMENT

(71) Applicant: The Board of Trustees of the Leland Stanford Junior University, Stanford, CA (US)

(72) Inventors: Jing-Hung Wang, Stanford, CA (US); Alexis Forterre, Stanford, CA (US); A. C. Matin, Stanford, CA (US); Alain Delcayre, San Jose, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 310 days.

(21) Appl. No.: 16/649,083

(22) PCT Filed: Sep. 25, 2018

(86) PCT No.: PCT/US2018/052704
§ 371 (c)(1),
(2) Date: Mar. 19, 2020

(87) PCT Pub. No.: WO2019/067464
PCT Pub. Date: Apr. 4, 2019

(65) Prior Publication Data

US 2021/0161817 A1 Jun. 3, 2021

Related U.S. Application Data

(60) Provisional application No. 62/697,758, filed on Jul. 13, 2018, provisional application No. 62/564,217, filed on Sep. 27, 2017.

(51) Int. Cl.
*A61K 9/127* (2006.01)
*A61K 47/69* (2017.01)
(Continued)

(52) U.S. Cl.
CPC ........ *A61K 9/1271* (2013.01); *A61K 47/6911* (2017.08); *C07K 14/47* (2013.01);
(Continued)

(58) Field of Classification Search
None
See application file for complete search history.

(56) References Cited

U.S. PATENT DOCUMENTS

| | | | | |
|---|---|---|---|---|
| 2004/0197314 A1* | 10/2004 | Delcayre | C12N 15/62 | 424/93.21 |
| 2007/0254852 A1* | 11/2007 | Matin | C12N 9/0036 | 536/23.1 |

(Continued)

FOREIGN PATENT DOCUMENTS

| | | |
|---|---|---|
| WO | 2015002956 * | 1/2015 |
| WO | 2017201325 | 11/2017 |

*Primary Examiner* — Karl J Puttlitz
(74) *Attorney, Agent, or Firm* — Pamela J. Sherwood; Bozicevic, Field & Francis LLP

(57) ABSTRACT

Provided herein are extracellular vesicle (EV) (a.k.a. exosome) compositions for specifically targeting the delivery of a therapeutic agent to particular cells and/or tissues in a subject, as well as methods of making and methods of using said compositions. The compositions and methods disclosed herein are useful for targeted drug delivery in the treatment of diseases in which a cell surface receptor is overexpressed, such as, for example, cancer.

12 Claims, 13 Drawing Sheets

Specification includes a Sequence Listing.

(51) Int. Cl.
*C07K 14/47* (2006.01)
*C07K 16/32* (2006.01)
*C12N 9/02* (2006.01)
*C12N 15/88* (2006.01)
*C12N 15/62* (2006.01)
*A61K 39/00* (2006.01)

(52) U.S. Cl.
CPC ............ *C07K 16/32* (2013.01); *C12N 9/0036* (2013.01); *C12N 15/62* (2013.01); *C12N 15/88* (2013.01); *C12Y 106/05005* (2013.01); *A61K 2039/505* (2013.01); *C07K 2317/622* (2013.01); *C07K 2319/035* (2013.01); *C07K 2319/20* (2013.01); *C07K 2319/21* (2013.01); *C07K 2319/30* (2013.01)

(56) References Cited

U.S. PATENT DOCUMENTS

2015/0064215 A1* 3/2015 Huang .............. A61K 48/0025 435/320.1
2016/0184458 A1 6/2016 Heartlein

* cited by examiner

THERAPEUTIC AGENTS SPECIFICALLY DELIVERED BY EXOSOMES FOR CANCER TREATMENT

CROSS REFERENCE

This application is a 371 application and claims the benefit of PCT Application No. PCT/US2018/052704, filed Sep. 25, 2018, which claims benefit of U.S. Provisional Patent Application No. 62/564,217, filed Sep. 27, 2017 and U.S. Provisional Patent Application No. 62/697,758 filed Jul. 13, 2018, which applications are incorporated herein by reference in its entirety.

FEDERALLY SPONSORED RESEARCH AND DEVELOPMENT

This invention was made with Government support under contract TR000902 awarded by the National Institutes of Health. The Government has certain rights in the invention.

TECHNICAL FIELD

The present disclosure generally pertains to extracellular vesicle (EV) (a.k.a. exosome) compositions for specifically targeting therapeutic and/or active agents to particular cells and/or tissues in need of treatment with said therapeutic and/or active agent, as well as to methods of making and methods of using said compositions. The compositions and methods disclosed herein are useful for targeted drug delivery in the treatment of diseases in which a cell surface receptor is overexpressed, such as, for example, cancer.

BACKGROUND

Exosomes are small endosomally-derived membrane-based nanovesicles that are secreted by a variety of cell types into the extracellular environment following fusion of late endosomal multivesicular bodies with the plasma membrane. (See, e.g., Garin et al., 2001*, J. Cell Biol.* 152; 165-80). Cells from various tissue types have been shown to secrete exosomes, including dendritic cells, immune cells (e.g., B-cells and T cells), tumor cells, mast cells, and senescent cells. Exosomes from different cell types exhibit discrete sets of proteins and lipid moieties that reflect their cells of origin (See, e.g., Thery et al., 1999, 147:599-610; Thery et al., 2001*, J. Immunol.* 166:7309-18). Exosomes display proteins involved in antigen presentation (MHC Class I and MHC Class II) (Iero et al., 2008*, Cell Death Differ.* 15:80-88). Their main protein markers are tetraspanins (CD63, CD9), Alix, and TSG101, and they are able to mediate immune response by activating T cells (via antigen presentation); natural killer cells (via NKG2D ligand binding); and dendritic cells (via antigen transfer) (See, e.g., Thery et al., 2009*, Nat. Rev. Immunol.* 9:581-593). Exosomes are thought to be involved in cell-cell communication, leading to immune modulation.

Exosomes are predicted to be useful as drug delivery vehicles, and because exosomes have an extracellular membrane lipid bilayer composition similar to the body's own cells, they are believed to be non-immunogenic, offering advantages over nanoparticulate drug delivery systems such as liposomes and polymeric nanoparticles. Exosomes can be isolated using several different techniques, including centrifugation, ultrafiltration, size selection using HPLC, or using antibodies against exosome-associated antigens, such as cluster of differentiation (CD) molecules CD63, CD81, CD82, CD9, epithelial cell adhesion molecule (EpCAM), and Ras-related protein (RAB5), for example. Exosomes can be characterized based on their size, protein content, and lipid content. Exosomes range in size between approximately 40 to 100 nm, and are much smaller compared to other systems, such as microvesicles, which range from 100 to 500 nm. Several methods can be used to characterize exosomes, including flow cytometry, nanoparticle tracking analysis, dynamic light scattering, western blot, mass spectrometry, and microscopy techniques. Exosomes can also be characterized and marked based on their lipid or protein compositions, with integrins and tetraspanins being the two most abundant proteins found in exosomes. Other protein markers include TSG101, ALG-2 interacting protein X (ALIX), flotillin 1, and cell adhesion molecules. (See, for example, Ha, et al., (2016), *Acta Pharmaceutica Sinica B,* 6(4):287-296; See also Kanada, et al., (2015) *PNAS* E1433-1442).

Interestingly, exosomes can carry microRNA (miRNA) in cells. For example, exosomes have been used to deliver let-7a miRNA (which acts as a tumor suppressor that inhibits the malignant growth of cancer cells) to epidermal growth factor receptor (EGFR)-expressing breast cancer cells. Targeting was achieved by engineering the exosome donor cells to express the transmembrane domain of platelet-derived growth factor receptor fused to either the mature EGF peptide or an EGFR-specific GE11 peptide (GE11 peptide is known to be less mitogenic than EGF). When exosomes were intravenously injected, they delivered let-7a miRNA to EGFR-expressing xenograft breast cancer tissue in RAG2−/− mice. It was further observed that the GE-11 positive exosomes did not stimulate EGFR signaling like the mature EGF peptide did. These results demonstrate that exosomes show promise as delivery vehicles for targeting EGFR-expressing cancerous breast tissue with the let-7a miRNA. (Ohno, et al., (2013) *Molecular Therapy.* 21(1): 185-191).

A significant challenge for current drug delivery technologies is that many of the newer drug candidates such as proteins and nucleic acids are highly unstable inside in vivo environment. Because of their small size and lipid bilayer composition, exosomes can avoid phagocytosis or degradation by macrophages and can also circulate for extended periods of time within the body. Unlike typical nanoparticulate systems such as liposomes or polymeric nanoparticles, exosomes may avoid the endosomal pathway and lysosomal degradation, and also deliver cargoes directly into the cytoplasm. By virtue of avoiding the endosomal pathway transfection efficiency for molecules such as siRNA might be enhanced. Exosomes are naturally stable and their targeting properties might be exploited by changing the composition of the exosomes. Another significant advantage of these drug delivery vehicles also includes their ability to cross the blood-brain barrier (BBB). However, many challenges remain (e.g., assembly and drug loading) in the development of exosomes as vehicles for therapeutic and/or bioactive cargo and drug delivery. Furthermore, purification and isolation of exosomes with high purity remains problematic. The isolation methods yield low quantities of exosomes and their large scale production for clinical studies and post drug approval is expensive. Finally, because exosomes comprise heterogeneous components, they may exhibit immunogenicity (immunostimulatory or immunosuppressive effects) based on nature of parental donor cells. (Ha, et al., (2016), *Acta Pharmaceutica Sinica B,* 6(4)287-296; Kanada, et al., (2015) *PNAS* E1433-1442).

Chemotherapy is widely used in treatment of diseases such as cancer, but conventional approaches often lack selectivity for diseased tissues and/or cells rather than normal tissues/cells. Furthermore, some chemotherapeutic agents are ineffective, for example, in treating certain cancer types, including many common solid tumors, a failure due, in part, to the intrinsic or acquired drug resistance of many tumor cells. Another drawback to the use of chemotherapeutic agents is the severity of side effects, including bone marrow suppression, nausea, vomiting, hair loss, and ulcerations in the mouth and other mucosal tissues. Given these disadvantages (lack of selectivity, insufficient drug concentration in specific tissues/cells, development of drug-resistance, and severe, non-specific and global side effects), there remains a long-felt need for new therapeutic compositions and methods for treating cancer and other diseases.

Reductive prodrugs are compounds that are nontoxic in their native form, but produce a highly toxic species when reduced. These drugs kill by generating DNA adducts and can target both growing and non-growing tumor cells, which is advantageous since in human tumors, generally only a small fraction of cells is actively replicating at a given time. Reductive prodrug cancer chemotherapy using compounds such as MMC and CB1954 owes its rationale to the fact that the concentration of the enzymes that reduce them, such as mammalian DT-diaphorase (NQO1), increases in tumor cells. This makes the tumor cells more potent reducers of these drugs, and therefore more susceptible to their killing effect. However, these enzymes are present also in normal mammalian cells, and while their activity is lower in such cells than in tumor cells, it is high enough to produce severe side effects.

An approach to preferentially killing pathological cells, most widely used for treating cancer, is to introduce a gene into the target cells that encodes an enzyme capable of converting a prodrug of relatively low toxicity into a potent cytotoxic drug. Systemic administration of the prodrug is then tolerated since it is only converted into the toxic derivative locally, for example in a tumor, by cells expressing the prodrug-converting enzyme. This approach is known as gene-directed enzyme prodrug therapy (GDEPT), or when the gene is delivered by means of a recombinant viral vector, virus-directed prodrug therapy (VDEPT) (McNeish et al., 1997). A class of enzymes that has been well studied in GDEPT is bacterial nitroreductases (NTRs), such as NfsA and NfsB from *Escherichia coli*. These enzymes can reduce several nitro substituted organic compounds.

An example of an enzyme/prodrug system employs nitroreductase and the aziridinyl prodrug CB1954 (5-aziridinyl-2,4-dinitrobenzamide) (Knox et al., 1988). CB1954 (also known as Tretazicar) is an anticancer prodrug that can be activated by the enzyme NAD(P)H quinone oxidoreductase 2 (NQO2) and converted in the presence of NQO2 and co-substrate caricotamide (EP-0152R) (EP) into a potent cytotoxic bifunctional alkylating agent. However, CB1954 is a poor substrate for the human nitroreductase, and so GDEPT was conceived as a way of introducing a suitable nitroreductase, preferably with greater activity against CB1954, in order to sensitize targeted cells. A bacterial (*E. coli*) nitroreductase has been widely used for this purpose.

While such developments in targeted biological therapies hold tremendous potential for the treatment of disease, their effective use remains limited. There exists a need for a local therapy that provides for effective killing of pathological cells. The present disclosure addresses this need.

BRIEF SUMMARY

In some aspects, provided herein is a therapeutic composition comprising an extracellular-receptor-targeted exosome presenting a targeting moiety on its surface, wherein the exosome comprises: (a) a chimeric protein comprising: i) a leader sequence (LS) for migration of the chimeric protein to the exosome surface, ii) a targeting moiety having high affinity for an extracellular receptor overexpressed in a disease, iii) a lactadherin C1-C2 domain, and iv) an epitope tag for purification, and (b) an active agent included/loaded into the exosome.

In some embodiments, the active agent in the exosome is a nucleic acid, such as an interfering RNA or an mRNA. In some embodiments, the active agent loaded into the exosome is selected from a DNA, an RNA, an mRNA, an siRNA or miRNA, a polypeptide/protein, an antibiotic, a prodrug and a small molecule compound. In some embodiments, the active agent is an mRNA. In some embodiments, the mRNA encodes an enzyme that converts a prodrug to a drug. In some embodiments, the enzyme is ChrR.

In some embodiments, the prodrug is selected from a dinitrobenzamide, a nitroaniline-based alkylating agent, and a quinone.

In some embodiments, the prodrug is selected from the group consisting of: 6-chloro-9-nitro-5-oxo-5H-benzo-(a)-phenoxazine (CNOB); 2,5-diaziridinyl-3-(hydroxymethyl)-6-methyl-1,4-benzoquinone; 5-aziridinyl-2,4-dinitrobenzamide (CB 1954); 1,4-bis[[2-(dimethylamino) ethyl]amino]-5,8-dihydroxyanthracene-9,10-dione (AQ4); SN 23862; SN 27217; mitomycin C; 17-allylamino-17-demethoxygeldanamycin (17-AAG); and combinations thereof.

In some embodiments, the targeting moiety is an antibody or functional fragment thereof (e.g., scFv). In some embodiments, the targeting moiety is an extracellular receptor-targeting scFv antibody. In some embodiments, the active agent is a polypeptide. In some embodiments, the active agent is a small molecule.

In some embodiments, an enzyme that converts the prodrug to a lethal drug is co-administered. In some embodiments, an enzyme that converts a prodrug to a lethal drug is loaded into the exosomes.

In some aspects, provided herein is a method of producing an extracellular-receptor-targeted exosome, said method comprising (a) transfecting eukaryotic cells with an expression construct that expresses the chimeric protein described herein, (b) isolating exosomes from the cells, and (c) including/loading a therapeutic agent into the exosome.

In some aspects, provided herein is a method of treating or ameliorating a disease or disorder in which an extracellular receptor is overexpressed, comprising administering to a subject in need thereof a composition comprising the extracellular receptor-targeted exosomes described herein.

In some embodiments, the disease is a hyperproliferative disorder, such as cancer. These and other objects, advantages, and features of the disclosure will become apparent to those persons skilled in the art upon reading the details of the compositions and methods as more fully described below.

In some aspects, provided herein is a method of producing an extracellular-receptor-targeted exosome, the method comprising transfecting eukaryotic cells with an expression construct that expresses the chimeric protein described herein; isolating exosomes; and loading an active agent into the exosomes.

In some embodiments of the method, the active agent is selected from a DNA, an RNA, an mRNA, an siRNA or miRNA, a polypeptide/protein, an antibiotic, and a small molecule compound. In some embodiments of the method, the active agent is an mRNA.

In some embodiments of the method, the mRNA encodes an enzyme that converts a prodrug to a drug. In some embodiments of the method, the enzyme is ChrR.

In some embodiments of the method, the prodrug is selected from the group consisting of: 6-chloro-9-nitro-5-oxo-5H-benzo-(a)-phenoxazine (CNOB); 2,5-diaziridinyl-3-(hydroxymethyl)-6-methyl-1,4-benzoquinone; 5-aziridinyl-2,4-dinitrobenzamide (CB 1954); 1,4-bis[[2-(dimethylamino) ethyl]amino]-5,8-dihydroxyanthracene-9,10-dione (AQ4); SN 23862; SN 27217; mitomycin C; 17-allylamino-17-demethoxygeldanamycin (17-AAG); and combinations thereof.

In some embodiments of the method, the targeting moiety in the chimeric protein is an extracellular receptor-targeting antibody or functional fragment thereof (e.g., scFv).

In some embodiments of the method, the active agent is selected from a polypeptide, an antibiotic, an siRNA or miRNA, and a small molecule.

BRIEF DESCRIPTION OF THE DRAWINGS

The present disclosure will be better understood upon a reading of the following detailed description in conjunction with the accompanying drawings. According to common practice, the various features of the drawings are not to-scale. On the contrary, the dimensions of the various features are arbitrarily expanded or reduced for clarity. The accompanying drawings show as follows:

FIG. 2A shows a schematic representation of the HER2 receptor-targeting ML39 chimeric protein (EVHB). FIG. 2B shows a NanoSight nanoparticle analysis of the EVs, where concentration of particles/ml is plotted vs. size (nm). FIG. 2C shows Western blots of extracted protein from EVs or whole cells of HEK293 cells transfected with pEVC1C2HER plasmid, or the empty plasmid (p6mLSC1C2; control. FIG. 2D shows the predicted protein structure of EVHB, including the ML39 scFv antibody, the leader sequence, and the C1 and C2 domains.

FIG. 3A shows ELISA detection of HER2 receptor binding activity of directed EVs (displaying EVHB) obtained from pEVC1C2HER plasmid-transfected HEK293 cells and of naïve EVs obtained from non-transfected HEK293 cells incubated with pure EVHB.

FIG. 3B is a schematic representation of EVHB display by EVs from HEK 293 cells (upper left cell containing organelles). The left panel labeled "Transfection" shows cells transfected with pEVC1C2HER plasmid, and EVs obtained from them, with an enlarged EV showing the membrane bilayer. The right panel labeled "Reconstitution" shows non-transfected cells after incubation with pure EVHB which is inserted into the membrane bilayer. FIG. 3C shows representative fluorescent and phase contrast images of corresponding regions showing the CFSE-labeled directed EV binding to BT474 cells and not to MCF7 cells. FIG. 3D shows directed EV binding to cells as determined by flow cytometry. Left panel of this figure shows the fluorescence shift caused by the indicated cell types (or mixture). The shift due to SKBR3 cells is arbitrarily assigned a value of 1. Right panel of this figure shows a quantification of the relative shifts based on the data in the left panel.

FIG. 4A shows the design of XPort/HChrR6 plasmid and its features involved in mRNA packaging into EVs. FIG. 4B shows qPCR results and successful loading of EVs with HChrR6 mRNA. Endogenous EV miR-16 level was determined as control [the Ct value of mRNA corresponds to $2\times10^{-4}$ copy/EV]. FIG. 4C illustrates the in vitro effectiveness of EXO-DEPT EVs. BT474 cells ($3\times10^{4}$) treated with $8\times10^{8}$ EXO-DEPT EVs generated MCHB fluorescence upon CNOB treatment, naïve EVs alone, or loaded but non-directed EVs (not displaying EVHB) show only background fluorescence upon CNOB treatment. FIG. 4D shows MCHB fluorescence normalized to cell viability. BT474 cells treated with EXO-DEPT EVs and CNOB generate MCHB fluorescence, and this was not affected by the presence of actinomycin D, but is eliminated in the presence of cyclohexamide (CHX). FIG. 4E shows the administration schedule of EVs and CNOB for in vivo test of the effect of EXO-DEPT EVs on orthotopically implanted BT474 tumors in nu/nu mice. FIG. 4F plots the average tumor volume for each treatment group. FIG. 4G shows the rate of tumor growth calculated from slopes of linear regression shown in Box and Whisker plot for each treatment group.

DETAILED DESCRIPTION

Figure 1:
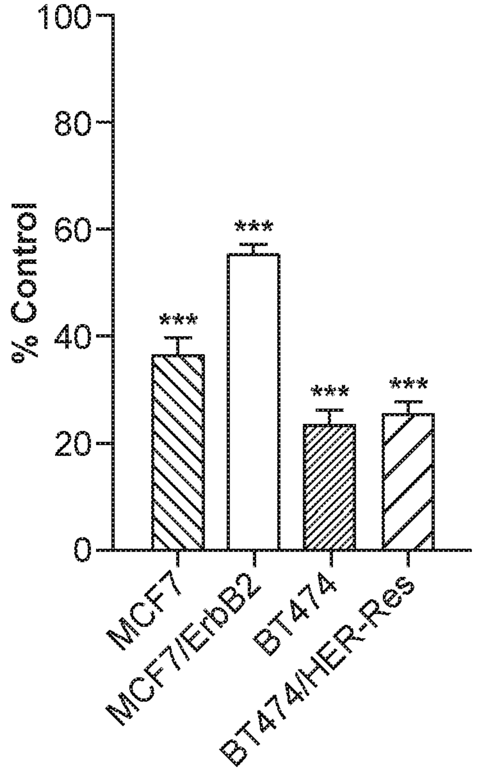
FIG. 1 shows the residual survival of cells after CNOB and ChrR6 treatment in vitro. Cell viability was determined by MTT assay. Data are presented as percent survival compared to untreated controls of the corresponding cells.

Before the present compositions and methods are further described, it is to be understood that this disclosure is not limited to particular embodiments of the composition or method described, and as such may, of course, vary. Other objects, features and advantages of the present disclosure will become apparent from the following detailed description. It should be understood, however, that the detailed description and specific examples, while indicating preferred embodiments of the disclosure, are given by way of illustration only, since various changes and modifications within the spirit and scope of the invention will become apparent to those skilled in the art from this detailed description. Furthermore, it is also to be understood that the terminology used herein is for the purpose of describing particular embodiments only, and is not intended to be limiting, as the scope of the present disclosure will be limited only by the appended claims.

The compositions and methods described herein are directed to targeted and loaded EXO-DEPT exosomes decorated with ligands that enable them to specifically target cells or tissues overexpressing a cell surface receptor, for specific delivery of therapeutic molecules (a specific drug, prodrug, gene and/or biomolecule such as mRNA, siRNA, proteins or small molecules), and methods for use of these exosomes in the treatment of cancer, a hyperproliferative disease or disorder, or other diseases in which specific extracellular receptors are overexpressed. The prodrug may comprise an activatable nitro moiety or reduced quinone, e.g. prodrugs in the dinitrobenzamide class. An activating enzyme, such as ChrR, may also be co-delivered by the exosome, or may be co-administered with the prodrug. The ChrR enzyme may be used in a native form, or in an improved form having enhanced enzyme kinetics for nitroreductase activity. In some embodiments the enzyme is provided to a patient in the form of a nucleic acid, where the enzyme is expressed in situ. The nucleic acid is optionally localized to the site of the cancer by physical means, or through the use of regulatable vectors having selective expression at the site of cancer or in cancer cells.

The present disclosure represents a new approach in the therapeutic regimen termed "Gene-delivered Enzyme Prodrug Therapy (GDEPT)," wherein mRNA is used (rather than DNA) for gene delivery, and exosomes are used as vehicles for the delivery and activation of a new prodrug. The composition and methods employ a new chimeric protein construct, termed EVHB, consisting of: i) leader sequence (LS) for EVHB migration to the exosome surface; ii) high affinity anti-HER2 scFv antibody to target the HER2 receptor; iii) lactadherin 01-02 domains, which bind to exosomes by interacting with their surface phosphatidylserine; and iv) His-tag, for EVHB purification. HEK293 cells transfected with the plasmid encoding this protein generate exosomes that express EVHB on their surface and have the capability of specifically targeting HER2-positive receptor, cells, and tumors (termed, "targeted" exosomes). These exosomes have also been loaded with exogenous mRNA, using the 'zipcode' technology that promotes mRNA entry into exosomes and a commercially available plasmid. The directed and loaded exosomes (called the "EXO-DEPT" exosomes) specifically deliver the mRNA to HER2-positive cells and tumors in mice. The mRNA encodes humanized and improved form of a bacterial enzyme, called HChrR6. This enzyme can convert a harmless prodrug, 6-chloro-9-nitro-5-oxo-5H-benzo-(a)-phenoxazine (CNOB), into the highly toxic drug, 9-p amino-6-chloro-5H-benzo'a"phenoxazine-5-one (MCHB). MCHB is strongly fluorescent and can be quantitated by its fluorescence intensity; it can also be visualized in living mice. As the mRNA is delivered specifically to the tumors, HChrR6 is generated specifically inside them. Consequently, the toxic drug, MCHB, is confined largely to the tumors attaining a high concentration inside them. Advantages of these innovations include the effective killing of cancer cells, avoidance of drug resistance, and prevention of damage to normal tissues. HChrR6 can also activate the prodrug CB1954, currently in clinical trials. Additionally, combined therapy with the two prodrugs can enhance the effectiveness of the treatment. The composition and methods described are generic and the anti-HER2 scFv in the EVHB construct can be easily replaced by another scFv (or other moieties) capable of targeting a different receptor; and the exosomes/EVs can be loaded with another mRNA, biomolecule and/or drug. Thus, the approach can be used for therapy of any disease in which a receptor is overexpressed. Examples of other receptors overexpressed in cancers are PSMA, bombasin, folate, transferrin, and sigma; many other diseases also overexpress specific receptors. (See, Wang, et al., (2016) *BMC Cancer* 16:524).

Definitions

Where a range of values is provided, it is understood that each intervening value, to the tenth of the unit of the lower limit unless the context clearly dictates otherwise, between the upper and lower limits of that range and any other stated or intervening value in that stated range, is encompassed and specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, some potential and preferred methods and materials are now described. All patents, patent applications and non-patent publications mentioned herein are incorporated herein by reference in their entirety to disclose and describe the methods and/or materials in connection with which the publications are cited. Unless mentioned otherwise, the techniques employed herein are standard methodologies well known to one of ordinary skill in the art. It is understood that the present disclosure supercedes any disclosure of an incorporated publication to the extent there is a contradiction. The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

It must be noted that as used herein and in the appended claims, the singular forms "a," "an," and "the" include plural referents unless the context clearly dictates otherwise. Thus, for example, reference to "an exosome" includes a plurality of such exosomes, and reference to "the therapeutic and/or active agent" includes reference to one or more agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The terms "individual," "subject," "host," and "patient," to which administration is contemplated, are used interchangeably herein; these terms typically refer to a vertebrate, preferably a mammal, including, but not limited to, rodents (mice, rats, etc.), simians, humans, mammalian farm animals, mammalian sport animals, and mammalian pets, but can also include commercially relevant birds such as chickens, ducks, geese, quail, and/or turkeys. A mammalian subject may be human or other primate (e.g., cynomolgus monkey, rhesus monkey), or commercially relevant mammals, farm animals, sport animals, and pets. such as cattle, pigs, horses, sheep, goats, cats, and/or dogs. The subject can be a male or female of any age group, e.g., a pediatric subject (e.g., infant, child, adolescent) or adult subject (e.g., young adult, middle-aged adult or senior adult). In some embodiments, the subject may be murine, rodent, lagomorph, feline, canine, porcine, ovine, bovine, equine, or primate. In some embodiments, the subject is a mammal. In some embodiments, the subject is a human. In some embodiments, the subject may be female. In some embodiments, the subject may be male. In some embodiments, the subject may be an infant, child, adolescent or adult.

As used herein, the terms "treatment," "treating," and the like, refer to obtaining a beneficial or desired pharmacologic and/or physiologic effect. For purposes of this disclosure, beneficial or desired effects include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. The treatment/effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease. "Treatment" can also mean prolonging survival as compared to expected survival if not receiving treatment. "Palliating" a disease means that the extent and/or undesirable clinical manifestations of a disease state are lessened and/or time course of the progression is slowed or lengthened, as compared to not administering the methods of the present disclosure.

A "therapeutically effective amount," an "effective amount," or "efficacious amount" means an amount sufficient to effect beneficial or desired clinical results. For example, an effective amount of a compound, when administered to a mammal or other subject for treating a disease, is sufficient to effect such treatment for the disease. The effective amount will vary depending on the compound, the disease and its severity and the age, weight, etc., of the subject to be treated. An effective amount can be administered in one or more administrations. For purposes of this disclosure, an effective amount of an enzyme in conjunction with a prodrug is an amount that is sufficient to palliate, ameliorate, stabilize, reverse, slow or delay the progression of the disease state.

The compositions disclosed herein may be administered through any mode of administration. In some aspects, the compositions may be administered intracranially. In some aspects, the compositions are suitable for parenteral administration. These compositions may be administered, for example, intraperitoneally, intravenously, or intrathecally. In some aspects, the compositions are injected intravenously. In some embodiments, the compositions may be administered enterally or parenterally. Compositions may be administered subcutaneously, intravenously, intramuscularly, intranasally, by inhalation, orally, sublingually, by buccal administration, topically, transdermally, or transmucosally. Compositions may be administered by injection. In some embodiments, compositions are administered by subcutaneous injection, orally, intranasally, by inhalation, or intravenously. In certain embodiments, the compositions disclosed herein are administered by subcutaneous injection.

The term "unit dosage form," as used herein, refers to physically discrete units suitable as unitary dosages for human and animal subjects, each unit containing a predetermined quantity of compounds/therapeutic agents of the present disclosure calculated in an amount sufficient to produce the desired effect in association with a pharmaceutically acceptable diluent, carrier or vehicle.

As used herein, the phrase "pharmaceutically acceptable carrier" refers to a carrier medium that does not interfere with the effectiveness of the biological activity of the active ingredient. Such a carrier medium is essentially chemically inert and nontoxic.

As used herein, the phrase "pharmaceutically acceptable" means approved by a regulatory agency of the Federal government or a state government, or listed in the U.S. Pharmacopeia or other generally recognized pharmacopeia for use in animals, and more particularly for use in humans.

As used herein, the term "carrier" refers to a diluent, adjuvant, excipient, or vehicle with which the therapeutic is administered. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier, if desired, can also contain minor amounts of wetting or emulsifying agents, or pH buffering agents. These pharmaceutical compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in Remington's Pharmaceutical Sciences by E. W. Martin. Examples of suitable pharmaceutical carriers are a variety of cationic polyamines and lipids, including, but not limited to N-(1(2,3-dioleyloxy)propyl)-N, N, N-trimethylammonium chloride (DOTMA) and diolesylphosphotidylethanolamine (DOPE). Liposomes are suitable carriers for gene therapy uses of the present disclosure. Such pharmaceutical compositions should contain a therapeutically effective amount of the compound, together with a suitable amount of carrier so as to provide the form for proper administration to the subject. The formulation should suit the mode of administration.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. These terms also include proteins that are post-translationally modified through reactions that include glycosylation, acetylation and phosphorylation.

As used herein, a "target cell" is a cell expressing an extracellular receptor on its surface. Tumor cells often overexpress such extracellular receptors. Usually a target cell is a mammalian cell, preferably a human cell. A "targeting moiety" having a high affinity for a receptor overexpressed in a disease state can be a binding protein (having a region, such as a complementarity determining region (CDR) that binds to a particular target receptor protein/polypeptide, or a fragment or epitope of the receptor), an antibody, or an antibody fragment (e.g., an scFv antibody). Examples of such targeting moieties include antibodies, such as a human antibody; a humanized antibody; a chimeric antibody; a recombinant antibody; a single chain antibody; a diabody; a triabody; a tetrabody; a Fab fragment; a F(ab') 2 fragment; an IgD antibody; an IgE antibody; an IgM antibody; an IgG1 antibody; an IgG2 antibody; an IgG3 antibody; or an IgG4 antibody, and fragments thereof. The binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the binding protein as well as wholly synthetic scaffolds comprising, for example, a biocompatible polymer. See, e.g., Korndorfer et al., 2003, *Proteins: Structure, Function, and Bioinformatics,* 53(1):121-129 (2003); Roque et al., *Biotechnol. Prog.* 20:639-654 (2004). In addition, peptide antibody mimetics ("PAMs") can be used, as well as scaffolds based on antibody mimetics utilizing fibronectin components as a scaffold. In the context of the present disclosure, a targeting moiety is said to specifically bind or selectively bind to the target when the dissociation constant (KO) is $\leq 10^{-8}$ M. The targeting moiety may specifically bind the target with high affinity when the $K_D$ is $\leq 10^{-9}$ M or $K_D$ is $\leq 10^{-1o}$ M. In some embodiments, the targeting moiety (e.g., scFv or antibody fragment) may bind to the target receptor or epitope with a $K_D$ of between about $10^{-7}$ M and about $10^{12}$ M. In some embodiments, the targeting moiety may bind with a $K_D$ of 1-2×$10^{-9}$ M.

The term "antibody" and "immunoglobulin" or "Ig" are used interchangeably herein, and is used in the broadest sense and specifically covers, for example, individual monoclonal antibodies (including agonist, antagonist, neutralizing antibodies, full length or intact monoclonal antibodies), anti-receptor antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain anti-receptor antibodies, and fragments of anti-receptor antibodies, as described below. An antibody can be human, humanized, chimeric and/or affinity matured as well as an antibody from other species, for example mouse, rabbit etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See, Borrebaeck (ed.) (1995) Antibody Engineering, Second Ed., Oxford University Press.; Kuby (1997) Immunology, Third Ed., W.H. Freeman and Company, New York). In specific embodiments, the specific molecular antigen can be bound by an antibody provided herein includes a receptor polypeptide, receptor fragment or receptor epitope. Antibodies also include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments (e.g., antigen-binding fragments such as receptor binding fragments) of any of the above, which refers a portion of an antibody heavy or light chain polypeptide that retains some or all of the binding activity of the antibody from which the fragment was derived. Non-limiting examples of functional fragments (e.g., antigen-binding fragments such as receptor binding fragments) include single-chain Fvs (scFv) (e.g., including monospecific, bispecific, etc.), Fab fragments, F(ab') fragments, F(ab)2 fragments, F(ab)2 fragments, disulfide-linked Fvs (sdFv), Fd fragments, Fv fragments, diabody, triabody, tetrabody and minibody. In particular, antibodies provided herein include immunoglobulin molecules and immunologically active portions of immunoglobulin molecules, for example, antigen binding domains or molecules that contain an antigen-binding site that binds to a receptor antigen (e.g., one or more complementarity determining regions (CDRs) of an anti-receptor antibody). Such antibody fragments can be found described in, for example, Harlow and Lane, Antibodies: A Laboratory Manual, Cold Spring Harbor Laboratory, New York (1989); Myers (ed.), Molec. Biology and Biotechnology: A Comprehensive Desk Reference, New York: VCH Publisher, Inc.; Huston et al., *Cell Biophysics,* 22:189-224 (1993); Plückthun and Skerra, *Meth. Enzymol.,* 178:497-515 (1989) and in Day, E.D., Advanced Immunochemistry, Second Ed., Wiley-Liss, Inc., New York, N.Y. (1990). The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. As used herein, antibodies may also be agonistic antibodies or antagonistic antibodies.

The term "gene" is well understood in the art and includes polynucleotides encoding a polypeptide or a functional polynucleotide. In addition to the polypeptide coding regions, a gene may include non-coding regions including, but not limited to, introns, transcribed but untranslated segments, and regulatory elements upstream and downstream of the coding segments.

The terms "nucleic acid" and "polynucleotide" are used interchangeably herein, and refer to a polymeric form of nucleotides of any length, either deoxyribonucleotides or ribonucleotides, or analogs thereof. Non-limiting examples of nucleic acids and polynucleotides include linear and circular nucleic acids, messenger RNA (mRNA), cDNA, recombinant polynucleotides, vectors, probes, primers, single-, double-, or multi-stranded DNA or RNA, genomic DNA, DNA-RNA hybrids, chemically or biochemically modified, non-natural, or derivatized nucleotide bases, oligonucleotides containing modified or non-natural nucleotide bases (e.g., locked-nucleic acids (LNA) oligonucleotides), and interfering RNAs.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi(dot)nlm(dot)nih(dot) gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

The terms "double stranded RNA," "dsRNA," "partial-length dsRNA," "full-length dsRNA," "synthetic dsRNA," "in vitro produced dsRNA," "in vivo produced dsRNA," "bacterially produced dsRNA," "isolated dsRNA," and "purified dsRNA" as used herein refer to nucleic acid molecules capable of being processed to produce a smaller nucleic acid, e.g., a short interfering RNA (siRNA), capable of inhibiting or down regulating gene expression, for example by mediating RNA interference "RNAi" or gene silencing in a sequence-specific manner. Design of a dsRNA or a construct comprising a dsRNA targeted to a gene of interest is routine in the art, See e.g., Timmons et al. (2001) *Gene,* 263:103-112; Newmark et al. (2003) *Proc Natl Acad Sci USA,* 100 *Supp* 1:11861-5; Reddien et al. (2005) *Developmental Cell,* 8:635-649; Chuang & Meyerowitz (2000) *Proc Natl Acad Sci USA,* 97:4985-90; Piccin et al. (2001) *Nucleic Acid Res,* 29:E55-5; Kondo et al. (2006) *Genes Genet Syst,* 81:129-34; and Lu et al. (2009) *FEBS J,* 276: 3110-23; the disclosures of which are incorporated herein by reference.

The terms "short interfering RNA", "siRNA", and "short interfering nucleic acid" are used interchangeably may refer to short hairpin RNA (shRNA), short interfering oligonucleotide, short interfering nucleic acid, short interfering modified oligonucleotide, chemically-modified siRNA, post-transcriptional gene silencing RNA (ptgsRNA), and other short oligonucleotides useful in mediating an RNAi response. In some instances siRNA may be encoded from DNA comprising a siRNA sequence in vitro or in vivo as described herein. When a particular siRNA is described herein, it will be clear to the ordinary skilled artisan as to where and when a different but equivalently effective interfering nucleic acid may be substituted, e.g., the substation of a short interfering oligonucleotide for a described shRNA and the like.

"Complementary," as used herein, refers to the capacity for precise pairing between two nucleotides of a polynucleotide (e.g., an antisense polynucleotide) and its corresponding target polynucleotide. For example, if a nucleotide at a particular position of a polynucleotide is capable of hydrogen bonding with a nucleotide at a particular position of a target nucleic acid, then the position of hydrogen bonding between the polynucleotide and the target polynucleotide is considered to be a complementary position. The polynucleotide and the target polynucleotide are complementary to each other when a sufficient number of complementary positions in each molecule are occupied by nucleotides that can hydrogen bond with each other. Thus, "specifically hybridizable" and "complementary" are terms which are used to indicate a sufficient degree of precise pairing or complementarity over a sufficient number of nucleotides such that stable and specific binding occurs between the polynucleotide and a target polynucleotide.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense polynucleotide which is 18 nucleotides in length having four noncomplementary nucleotides which are flanked by two regions of complete complementarity with the target nucleic acid would have 77.8% overall complementarity with the target nucleic acid. Percent complementarity of an oligomeric compound with a region of a target nucleic acid can be determined routinely using BLAST programs (basic local alignment search tools) and PowerBLAST programs known in the art (Altschul et al., *J. Mol. Biol.,* 1990, 215, 403-410; Zhang and Madden, *Genome Res.,* 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.,* 1981, 2, 482-489).

As used herein, "cytotoxicity" is a term well understood in the art and refers to a state in which one or more of a cell's usual biochemical or biological functions are perturbed. These activities include, but are not limited to, metabolism, cellular replication, DNA replication, transcription, translation, and uptake of molecules. "Cytotoxicity" includes cell death and/or cytolysis. Assays are known in the art which indicate cytotoxicity, such as dye exclusion, 3H-thymidine uptake, and plaque assays. The term "selective cytotoxicity", as used herein, refers to the cytotoxicity conferred by an enzyme in conjunction with a prodrug on a target cell, compared to the cytotoxicity conferred by the prodrug in the absence of the bacterial enzyme. Such cytotoxicity may be measured, for example, by plaque assays, reduction or stabilization in size of a tumor comprising target cells, or the reduction or stabilization of serum levels of a marker characteristic of the tumor cells or a tissue-specific marker, e.g., a cancer marker such as prostate specific antigen or tumor reduction size using firefly luciferase expressing tumor cells to allowing visualization in situ of the target cells.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

The term "prodrug" refers to a compound that is converted via one or more enzymatically catalyzed steps into an active compound that has an increased pharmacological activity relative to the prodrug. The term "drug" and "active drug" refer to the active moieties of a prodrug. After chemical modification by an enzyme such as ChrR, the active drug acts therapeutically upon the targeted tumor cell. In another example, the prodrug is chemically modified by the activating enzyme, for example, by oxidation, reduction, phosphorylation, dephosphorylation, the addition of a moiety, or the like.

Prodrugs of interest for the methods disclosed herein may comprise one or more nitro groups, which groups are acted upon by the enzyme ChrR to generate an active form of the drug. Examples of such prodrugs include those of the dinitrobenzamide and the quinone based classes. Such drugs include, without limitation, 2,5-diaziridinyl-3-(hydroxymethyl)-6-methyl-1,4-benzoquinone; 5-aziridinyl-2,4-dinitrobenzamide (CB 1954); 1,4-bis[[2-(dimethylamino) ethyl] amino]-5,8-dihydroxyanthracene-9,10-dione (AQ4), the dinitrobenzamide mustard compound SN 23862 and related amide-substituted mustard SN 27217; nitroaniline-based alkylating agents as described in U.S. patent application 20050256191 (herein incorporated by reference for the teaching of such prodrugs); mitomycin C, 17-allylamino-17-demethoxygeldanamycin (17-AAG), and the like. (See, Wang, et al., (2016) *BMC Cancer* 16:524).

As used herein, the terms "neoplastic cells", "neoplasia", "transformed", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation. Neoplastic cells can be malignant or benign.

A hyperproliferative disease, disorder and/or condition, as used herein, often refers to cancer. The term "cancer" usually denotes malignant cell populations. Such hyperproliferative disorders have an excess cell proliferation of one or more subsets of cells, which often appear to differ from the surrounding tissue both morphologically and genotypically. The excess cell proliferation can be determined by reference to the general population and/or by reference to a particular patient, e.g. at an earlier point in the patient's life. Hyperproliferative cell disorders can occur in different types of animals and in humans, and produce different physical manifestations depending upon the affected cells.

Cancers include leukemias, lymphomas (Hodgkins and non-Hodgkins), sarcomas, melanomas, adenomas, carcinomas of solid tissue including breast cancer and pancreatic cancer, hypoxic tumors, squamous cell carcinomas of the mouth, throat, larynx, and lung, genitourinary cancers such as cervical and bladder cancer, hematopoietic cancers, head and neck cancers, and nervous system cancers, such as gliomas, astrocytomas, meningiomas, etc., benign lesions such as papillomas, and the like.

The terms "exosome" or "extracellular vesicle" refer to small (<about 500 nm, and preferably between approximately 40 to 100 nm in diameter) lipid bilayer membrane-based nanovesicles derived from the endosomal secretory pathway in cells. These exosomes can be isolated or derived from a wide variety of eukaryotic cells (e.g., neurons, tumor cells, kidney cells), or can be isolated from cells engineered to express a particular chimeric protein expression construct as described in the present disclosure. (See Kalani, et al., (2014) *Mol. Neurobiol.* 49(1):590-600).

The term "lactadherin" (also known as milk fat globule-EGF factor 8, or MFG-E8) refers to a peripheral membrane glycoprotein expressed abundantly in lactating mammary glands and secreted in association with fat globules. Lactadherin consists of two repeated EGF-like domains (C-domains, C1 and C2), and contains an integrin-binding motif (RGD sequence) in the EGF-like domain. "C1 domain" and "C2 domain" or "C1/C2 domain" refer to the domains found within the lactadherin protein which appear to be responsible for membrane association, interacting with a surface phosphatidylserine. (See Oshimsa, et al., (2002) *Eur. J. Biochem.* 269:1209-1218). Lactadherin also comprises a leader sequence (LS) for migration of the expressed protein to the exosome surface.

The approach described herein entails the use of a compound that is inert to native human enzymes and is largely harmless, but upon activation by an enzyme encoded by a foreign gene of viral or bacterial origin, is converted into a cytotoxic drug. Provided that the gene can be specifically targeted to tumors, this therapy offers the possibility of confining the drug to the tumor at a high concentration, and mitigating off-target effects. The present disclosure is directed to specific targeting of the GDEPT regimen, namely, 6-chloro-9-nitro-5-oxo-5H-benzo-(a)-phenoxazine (CNOB) or CB1954/HChrR6 to HER2-overexpressing breast cancer. HChrR6 is an *Escherichia* coif enzyme that was discovered, improved and humanized; it converts CNOB into the cytotoxic drug, 9-p amino-6-chloro-5H-benzo[a]phenoxazine-5-one (MCHB). The latter is strongly fluorescent at a wavelength that can be imaged in living mice, and quantitated by its fluorescence intensity, facilitating characterization of this GDEPT. MCHB causes DNA intercalation, and is thus likely to kill both growing and non-growing cells, which is advantageous, as a significant portion of tumor cells is typically quiescent. It has an impressive bystander effect (BE)-BE refers to the leakage of the cytotoxic drug from the transfected tumor cells that also kills the neighboring non-transfected tumor cells, and is critical for the effectiveness of GDEPT, as no method of gene delivery can transfect all the cells in a tumor.

To determine the in vivo efficacy of this regimen in these initial studies, the issue of specific targeting was avoided by using 4T1 murine mammary cells that endogenously generated HChrR6 enzyme to implant tumors in mice; marked improvement was seen in the survival of mice treated with CNOB. To develop a targeting strategy, HER2-positive breast cancer was chosen. This disease is associated with poor clinical outcomes. HER2 is part of the type 1 receptor tyrosine kinase signaling network that regulates growth and differentiation; dysregulation of this network by HER2 gene amplification results in cancer. The marked increase in HER2 receptor has been exploited to design effective targeted therapies, e.g., trastuzumab and Lapatinib, for treating this disease. The same feature made it an attractive model system for us to design the above-mentioned new treatment for this cancer.

Viruses have commonly been used for gene delivery in GDEPTS, but raise concerns of immune recognition, insertional mutagenesis, and inflammatory toxicity. Extracellular vesicles (EVs, also called exosomes) were used instead. These are small; consist of lipid bilayers; are constitutively generated by most body cells; are largely nontoxic; and can deliver their cargo directly into the cytoplasm, avoiding the endosomal pathway and lysosomal degradation. Their small size mitigates uptake by the reticuloendothelial system, and permits extravasation through vessel fenestrations present in tumors. As means of intracellular communication, they may be minimally immunogenic, especially when derived from mesenchymal stem cells or from patient's own, e.g., dendritic cells.

Herpes simplex virus Type 1 thymidine kinase and ganciclovir (HSV-tk/GCV) GDEPT has been tested in a Phase III clinical trial for treating glioblastoma multiforme patients. No beneficial results were seen, perhaps attributable to low-level and short-lived gene expression; this factor has also contributed to the fact that three other prodrug regimens have not proceeded beyond Phase I/II stages. A possible reason for poor gene expression might be the use of DNA for gene delivery in these trials. To be effective, DNA must first be transported (for transcription) into the nucleus. This is a highly inefficient process: less than 0.01-0.1% of the DNA delivered into the cytoplasm of mammalian cells enters the nucleus. Moreover, as this transport occurs during nuclear membrane dissolution in mitosis, it is especially inefficient in tumors, where a significant portion of cells is typically quiescent. In the present disclosure, mRNA was used instead, as upon transfer to cytosol, it is directly translated, and eliminates the risk of insertional mutagenesis. Indeed, mRNA-based gene uptake was more efficient, and melanoma xenograft growth was retarded >2-fold more when mRNA instead of DNA was used for gene delivery.

Herein described is the finding that that EVs, directed to the HER2 receptor and loaded with HChrR6-encoding mRNA ("EXO-DEPT" EVs), used in conjunction with CNOB, specifically kill HER2-positive cells, and cause near-complete growth arrest of implanted orthotopic HER2-positive breast cancer tumors in mice. This is the first time that EVs have been successfully used to deliver exogenous functional mRNA to recipient cells and tumors. The approach described here is generic and can be used to treat any disease in which a marker is overexpressed.

The composition and methods described herein employ a new chimeric protein construct, termed EVHB, consisting of: i) lactadherin leader sequence (LS) for EVHB migration to the exosome surface; ii) high affinity anti-HER2 scFv antibody to target the HER2 receptor; iii) lactadherin C1-02 domains, which bind to exosomes by interacting with their surface phosphatidylserine (PS); and iv) His-tag, for EVHB purification. HEK293 cells transfected with the plasmid encoding this protein generate exosomes that express EVHB on their surface and have the capability of specifically targeting HER2-positive receptor, cells, and tumors (termed, "targeted" exosomes). These exosomes have also been loaded with exogenous mRNA, using the 'zipcode' technology that promotes mRNA entry into exosomes and a commercially available plasmid.

The directed and loaded exosomes (called the "EX©-DEPT" exosomes) specifically deliver the mRNA to HER2-positive cells and tumors in mice. The mRNA encodes humanized and improved form of a bacterial enzyme, called HChrR6. This enzyme can convert a harmless prodrug, 6-chloro-9-nitro-5-oxo-5H-benzo-(a)-phenoxazine (CNOB), into the highly toxic drug, 9-p amino-6-chloro-5H-benzo'a"phenoxazine-5-one (MCHB). MCHB is strongly fluorescent and can be quantitated by its fluorescence intensity; it can also be visualized in living mice. As the mRNA is delivered specifically to the tumors, HChrR6 is generated specifically inside them. Consequently, the toxic drug, MCHB, is confined largely to the tumors attaining a high concentration inside them. Advantages of these innovations include the effective killing of cancer cells, avoidance of drug resistance, and prevention of damage to normal tissues. HChrR6 can also activate the prodrug CB1954, currently in clinical trials. Additionally, combined therapy with the two prodrugs can enhance the effectiveness of the treatment.

mRNA can be delivered by a plasmid encoding the desired mRNA that is transcribed in the cell, or by delivery of mRNA itself. As an alternative to the use of a plasmid, mRNA encoding the prodrug activating enzyme can be generated by in vitro transcription, and used to load the EV directly with mRNA. In vitro transcription is a simple procedure that allows for template-directed synthesis of RNA molecules, based on the engineering of a template that includes a promoter sequence (e.g. from the T7 coliphage) upstream of the sequence of interest followed by transcription using the corresponding RNA polymerase.

The composition and methods described herein are generic and the anti-HER2 scFv in the EVHB construct can be easily replaced by another scFv (or other moieties) capable of targeting a different receptor; and the exosomes/EVs can be loaded with another mRNA, biomolecule and/or drug. Thus, the approach can be used for therapy of any disease in which a receptor is overexpressed. Examples of other receptors overexpressed in cancers are PSMA, bombasin, folate, transferrin, and sigma; many other diseases also overexpress specific receptors.

The present disclosure addresses and overcomes several problems with and limitations of other technologies. For example, the presently described compositions and method avoid the serious, highly painful and dangerous side effects that accompany most currently used chemotherapeutic approaches. Furthermore, the presently described compositions and methods enable specific gene/biomolecule/drug delivery to any disease in which a receptor is over expressed and that can benefit from such delivery. Improved drug-loading allows less drug overall to be delivered, which minimizes potential issues of drug toxicity or overexposure to the drug/agent outside the focal region of the brain one desires to treat, and minimizes the potential for side-effects.

The disclosure of U.S. Pat. No. 7,687,474 issued to Matin et al. (incorporated herein by reference in its entirety) is of interest with respect to the use of prodrugs to treat cancer. Disclosed therein are compositions and methods for treatment of diseases such as cancer, through administration to a patient of prodrugs comprising an activatable nitro moiety, e.g. prodrugs in the dinitrobenzamide class; or quinone based prodrugs reduced to the semiquinol or hydro-quinone form, e.g mytomicin C; and the activating *E. coli* enzyme NAD(P)H oxidoreductase ChrR (formerly called YieF). The ChrR enzyme may be used in a native form, or in improved forms having enhanced enzyme kinetics for reduction of quinones and nitro compounds. The U.S. Pat. No. 7,687,474 patent does not teach extracellular vesicles (EV) or exosomes.

U.S. Pat. No. 7,914,792, entitled "Methods and Compositions for Raising Antibodies and for Screening Antibody Repertoires" (with inventors Alain DELCAYRE and Jean-Bernard LE PECQ, and assigned to Exothera L.L.C., in Menlo Park, Calif.) discloses compositions and methods for raising antibodies generally comprising 1) providing highly immunogenic vesicles bearing at least one target antigen and 2) immunizing animals with the said antigen-bearing vesicles to induce antigen-specific antibody responses. The disclosure also presents methods of screening antibody repertoires comprising 1) providing vesicles bearing at least one target antigen and one marker and 2) isolating antibody-producing cells or particles with defined antigen specificity using the said antigen- and marker-bearing vesicles. Antibodies with defined antigen specificity can then be prepared from isolated antibody-producing cells using known methods of the art.

US Patent Application publication 2009/0148460, entitled "Exosome Ligands, their Preparation and Uses" (with inventors Alain DELCAYRE and Jean-Bernard LE PECQ) discloses exosome-specific ligands and compositions comprising the same. The disclosure also relates to methods of generating said ligands and compositions, to methods of using said ligands or compositions, e.g., to block the exosome pathway or to detect and/or characterize exosomes in a sample or subject, as well as to the antigens contacted by said ligands or compositions. The application can be used in experimental, research, therapeutic, prophylactic or diagnostic areas.

US Patent Application publication 2017/0051282, entitled "Extracellular Vesicle Methods and Compositions" (with inventors Thomas R. GINGERAS, Sudipto K. CHAKRABORTTY, Ashwin PRAKASH and Gal NECHOOSHTAN, all from Cold Spring Harbor, N.Y.) discloses compositions and methods of producing a therapeutic extracellular cancer vesicle (ECV) comprising an antisense masking oligonucleotide (AMO) having anti-tumor activity and specifically binds to a RNA fragment of a primary RNA transcript of the ECV, wherein the RNA fragment mediates tumor progression, comprising: (a) providing a cancer cell that can produce ECVs; (b) allowing the cancer cell to produce the ECUs; (c) transfecting an AMO in the ECVs; and (d) isolating exosomes produced by the cell, wherein the ECVs comprise the AMO bound to the RNA fragment of a primary RNA transcript.

US Patent Application publication 2017/0146542 and corresponding PCT Publication Wo 2016/0146542, entitled "Diagnostic Test for Early Stage Cancer" (having inventors Alan SCHROIT, Adi GAZDAR and E. Sally WARD OBER, and assigned to The Board of Regents of the University of Texas System) provides methods, compositions and kits for diagnosing various neoplastic diseases, especially at early, asymptomatic or metastatic stages. Even more particularly, it concerns diagnostic methods for the early detection of cancer by quantifying phosphatidylserine (PS)-expressing tumor-derived cancer exosomes in patient samples.

U.S. Pat. No. 8,686,115, entitled "Compositions and Methods for Quantitatively Monitoring Lipids" (having the sole inventor Wonhwa Cho and assigned to The Board of Trustees of the University of Illinois) is directed to fluorescent lipid binding proteins (FLBPs) comprising a lipid binding domain linked to a fluorophore, whereby the fluorophore's fluorescence emission undergoes a spectral change upon lipid binding, the fluorophore is selected from the group consisting of 2-dimethylamino-6-acyl-naphthalene (DAN) and RED fluorophore, and the lipid binding protein is selected from the group consisting of ENTH domain of epsin 1, C2 domain of bovine lactadherin, C 1B domain of protein kinase C-gamma, C2 domain of cytosolic phospholipase A2-beta, and PH domain of Bruton's tyrosine kinase PH.

U.S. Pat. No. 7,771,956, entitled "Method for Detecting the Presence of a Phospholipid" (with inventors Gary E. GILBERT, Jialan S H I, Christian W. HEEGAARD, and Jan T. RASMUSSEN, and assigned to Brigham & Women's Hospital, Inc. and United States of America Department of Veterans Affairs) discloses a method, kit and probe for detecting the presence of a phospholipid, such as phosphatidylserine, in a biological material, a binding agent including lactadherin, a fragment of lactadherin, a functional equivalent of lactadherin, or a functional equivalent of a fragment of a lactadherin, used to detect the presence of any phospholipid.

PCT Publication WO 03/076603, entitled "Vesicles Derived from T Cells, Production and Uses" (with inventors Yafei HOU, Di-Hwei HSU, Anita MEHTA-DAMANI, Henry LAMPARSKI, Pedro PAZ and Jean-Bernard LE PECQ, and assigned to Anosys, Inc. in Menlo Park, Calif.) describes compositions comprising vesicles released from activated T lymphocytes, and methods for their production and uses. Said vesicles contain a set of bioactive molecules which confer remarkable properties, such as antigen recognition, antigen presentation and other regulatory and effector functions. This disclosure also relates to methods for transferring or delivering antigenic molecules (e.g., peptides, peptide/MHC complexes, TCR or subunit thereof, etc.) to antigen presenting cells (APCs) using said vesicles, to induce specific immune responses, particularly specific CTL responses. The disclosure further relates to methods of delivering molecules selectively or specifically to target cells using said vesicles.

In some embodiments the prodrug produces a detectable product upon reduction, e.g. a fluorescent compound. The production of the drug from the prodrug can thus be imaged in vitro or in vivo. The tracking of the delivery vehicle and the prodrug provides for methods of in vivo analysis of cancer therapy.

In some embodiments, vectors comprising nucleic acid sequences (DNA or RNA) encoding HChrR6 are provided. Such vectors may provide for expression of the HChrR6 enzyme. Vectors of interest include plasmids, viruses capable of expression in mammalian cells, bacterial cells, and the like. In one embodiment, the vector is provided in an attenuated strain of *Salmonella typhimurium*. These bacteria have been shown to target both the aerobic and anaerobic zones of tumors, and do not infect normal tissues. In another embodiment, the vector is provided as a virus particle. In another embodiment, the vector, which may be present in a bacterial cell or viral coat, is provided in a pharmaceutical formulation. In another embodiment, the HChrR6 enzyme is delivered to cells, including fusion proteins comprising active HChrR6 enzyme, such as fusions with an immunoglobulin. In some embodiments, a nucleic acid encoding HChrR6 is provided within the exosome. In other embodiments, mRNA encoding HChrR6 is provided within the exosome.

ChrR Polypeptides

For use in the subject methods, the native ChrR protein from *E. coli*; homologs from related bacteria; variants derived therefrom; or a combination thereof may be used. The sequence of native *E. coli* ChrR is as follows: (SEQ ID NO:1) MSEKLQVVTL LGSLRKGSFN GMVARTLPKI APASMEVNAL PSIADIPLYD ADVQQEDGF PATVEA-LAEQI RQADGVVIVT PEYNYSVPGG LKNAIDWLSR LPDQPLAGKP VLIQTSSMGV IGGARCQYHL RQIL-VFLDAM VMNKPEFMGG VIQNKVDPQT GEVI-DQSTLD HLTGQLTAFG EFIQRVKI. The sequence is available at Genbank, accession number DQ989184.

Homologs of ChrR are known in the art, e.g. from such bacterium as *Shigella boydii; Salmonella enterica; Shigella flexneri; Salmonella typhimurium; Pseudomonas aeruginosa; Streptomyces coelicolor; Bacillus subtilis; Lactococcus lactis*, etc. Such homologs usually have at least about 35% amino acid identity with SEQ ID NO:1, more usually at least about 45% sequence identity; and may be at least about 80% sequence identity; at least about 85%, at least about 90%, or more. In some embodiments a fragment of a ChrR peptide may be utilized. Peptides of interest include fragments of at least about 50 contiguous amino acids, more usually at least about 100 contiguous amino acids, and may comprise 150 or more amino acids, up to the full length polypeptide. Fragments also included truncated forms of the polypeptide, where deletions may be from about 1 to about 5, to about 10, to about 15, to about 20, to about 25 amino acids, and may extend from residue 1 through 25 at either terminus of the polypeptide, comprising deletions of any length within the region; or may be at an internal location.

The sequence of the ChrR polypeptide may be altered in various ways known in the art to generate changes in sequence. The polypeptide will usually be substantially similar to the sequences provided herein, i.e. will differ by at least one amino acid, and may differ by at least two but not more than about ten amino acids. Where changes are introduced by shuffling or any other means of random mutation method, the amino acid differences may be greater. The sequence changes may be substitutions, insertions or deletions. Scanning mutations that systematically introduce alanine, or other residues, may be used to determine key amino acids.

In one embodiment, the polypeptide comprises an amino acid substitution at the position corresponding to amino acid 128 of SEQ ID N©:1. It will be understood by one of skill in the art that the corresponding amino acid can be determined in homologous polypeptides by alignment of the two sequences using conventional algorithms, e.g. BLASTN, CLUSTALW, and the like.

The native *E. coli* polypeptide contains a tyrosine at position 128, and substitutions of interest include an amino acid other than tyrosine at position 128. Substitutions of interest at this position include asn (asparagine), and amino acids that are conservative with respect to asn, including gln (glutamine). Other residues that commonly substitute for asparagine in homologous proteins include asp (aspartic acid); his (histidine); ser (serine); gly (glycine); lys (lysine); arg (arginine); glu (glutamine) and thr (threonine). A polypeptide with a tyr128asn substitution may be referred to as ChrR21.

In other embodiments, the polypeptide comprising an amino acid substitution at the position corresponding to amino acid 128 of SEQ ID NO:1 further comprises an amino acid substitution at the position corresponding to amino acid 150 of SEQ ID NO:1, where the substituted amino acid is other than glycine. Substitutions of interest include serine and amino acids that are conservative with respect to serine, including threonine, cysteine, and the like.

In other embodiments, the polypeptide comprising an amino acid substitution at the position corresponding to amino acid 128 of SEQ ID NO:1 may further comprise an amino acid substitution at the position corresponding to amino acid 154 of SEQ ID NO:1, where the substituted amino acid is other than asparagine. Substitutions of interest include threonine and amino acids that are conservative with respect to threonine, including serine, cysteine, and the like.

Modifications of interest that do not alter primary sequence, and which may be applied to the native sequence or to derivatives thereof include chemical derivatization of polypeptides, e.g., pegylation, acylation, acetylation, carboxylation, etc. Also included are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (See Friedler et al. (2000) *J. Biol. Chem.* 275:23783-23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art, or expressed from a polynucleotide construct. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In some embodiments, the ChrR enzyme is selected for enhanced cytotoxic activity in the presence of the nitro derivative or quinone based prodrugs such as CB 1954 and mitomycin C. In such screening assays, directed or non-directed mutations are introduced into the enzyme. Directed mutations include the use of various methods known in the art to introduce sequences into a targeted position, where the introduced sequences can comprise random sequences or can encode specific amino acids of interest. Non-directed mutations include the growth of cells in various mutagens, the use of error-prone PCR, and the like.

Nitroreductase enzymes can be screened indirectly for Cr(VI) reduction. For example the colorimetric diphenyl carbazide assay of Greenberg et a/(Greenberg, A. E., J. J. Connors, D. Jenkins, and M. A. Franson (ed.). 1981. Standard methods for the examination of water and wastewater, 15th ed., p. 187-190. American Public Health Association, Washington, D.C.) has been used. Alternatively the end product of chromate reduction can be determined using the X-ray absorption near-edge structure (XANES) spectrum. In this method, Cr(VI) and Cr(III) can be distinguished by the pronounced pre edge feature of the former. The fraction of Cr(VI) was calculated by dividing the height of the Cr(VI) pre edge peak by the total absorption; that of Cr(III) was calculated from the difference between the amount of chromium represented by the pre edge peak and the total absorption jump.

The enzymes thus screened, or new variants, may be screened in a direct method of detecting enhanced nitroreductase activity. Substrates of interest include those that produce a detectable product upon reduction, e.g. 6-chloro-9-nitro-5-oxo-5H-benzo[a]phenoxazine (CNOB), which is an analogue of CB 1954 in the nitro group being reduced. Reduction of CNOB generates a highly fluorescent compound (aminophenoxazine) and thus permits rapid and direct screening for prodrug-reducing activity. CNOB can also act as prodrug with the same efficiency as CB1954 in in vitro cytotoxicity assays. As its cytotoxic product is fluorescent, it can be monitored in vivo. The tracking of both the delivery vehicle and the prodrug provides for unique assays in vivo for cancer gene therapy.

Thus, in one embodiment of the disclosure, an assay is provided wherein the prodrug CNOB is administered to a patient or animal. The fluorescent product is used to monitor the efficacy of activation in an in vivo environment. In some embodiments, a laboratory animal is used in such a method, e.g. mouse, rat, rabbit, etc. In other embodiments, a human patient is treated in such a method.

ChrR Nucleic Acids

The disclosure includes nucleic acids that encode the sequence set forth in SEQ ID NO:1 and variants or homologs thereof, particularly variants or homologs encoding an amino acid substitution at positions 128; 150 and/or 154; nucleic acids that hybridize under stringent conditions, particularly conditions of high stringency, to the sequences that encode the sequence set forth in SEQ ID NO:1; and fragments and derivatives thereof. For example, the native sequence encoding SEQ ID NO:1 may be accessed at GenBank, accession no. NC_000913.2. One of skill in the art will readily appreciate that the redundancy of the genetic code allows many silent changes to be made in the coding sequence. Other nucleic acid compositions contemplated by and within the scope of the present disclosure will be readily apparent to one of ordinary skill in the art when provided with the disclosure here.

The nucleic acids of the disclosure include nucleic acids having sequence similarity or sequence identity to sequences that encode the sequence set forth in SEQ ID NO:1. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under stringent conditions, for example, at 50° C. or higher and 0,1×SSC (9 mM saline/0.9 mM sodium citrate). Hybridization methods and conditions are well known in the art, See, e.g., U.S. Pat. No. 5,707,829. Nucleic acids that are substantially identical to the provided nucleic acid sequence, e.g. allelic variants, homologs, genetically altered versions of the gene, etc., bind to sequences that encode the sequence set forth in SEQ ID NO:1 under stringent hybridization conditions. By using probes, particularly labeled probes of DNA sequences, one can isolate homologous or related genes. The source of homologous genes can be any species, e.g. primate species, particularly human; rodents, such as rats and mice; canines, felines, bovines, ovines, equines, fish, yeast, nematodes, etc.

Nucleic acids of the disclosure also include naturally occurring variants of the nucleotide sequences (e.g., degenerate variants, allelic variants, etc.). Variants of the nucleic acids of the disclosure are identified by hybridization of putative variants with nucleotide sequences disclosed herein, preferably by hybridization under stringent conditions. For example, by using appropriate wash conditions, variants of the nucleic acids of the disclosure can be identified where the allelic variant exhibits at most about 25-30% base pair (bp) mismatches relative to the selected nucleic acid probe. In general, allelic variants contain 15-25% bp mismatches, and can contain as little as even 5-15%, or 2-5%, or 1-2% bp mismatches, as well as a single bp mismatch.

The disclosure also encompasses homologs corresponding to the sequences that encode the sequence set forth in SEQ ID NO:1, where the source of homologous genes can be any species, particularly bacterial species, e.g. gram negative bacteria, particularly Enterobacteriaceae.

A genomic sequence of interest comprises the nucleic acid present between the initiation codon and the stop codon. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' and 3' end of the transcribed region. The nucleic acid compositions of the subject disclosure can encode all or a part of the subject polypeptides. Double or single stranded fragments can be obtained from the DNA sequence by chemically synthesizing oligonucleotides in accordance with conventional methods, by restriction enzyme digestion, by PCR amplification, etc. Isolated nucleic acids and nucleic acid fragments of the disclosure comprise at least about 18, about 50, about 100, to about 500 contiguous nt selected from the nucleic acid sequence.

The nucleic acids of the subject disclosure are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the disclosure can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the disclosure can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Expression Constructs

In the present methods, ChrR may be produced by recombinant methods. The DNA encoding ChrR polypeptide may be obtained from any library prepared from suitable cells, prepared from various sources according to the desired ChrR. The ChrR polypeptide-encoding gene may also be obtained by oligonucleotide synthesis. As described above, there are many ChrR-related polypeptides and genetic sequences known in the art. Libraries may be screened with probes (such as antibodies to the ChrR polypeptide, or oligonucleotides of about 20-80 bases) designed to identify the gene of interest or the protein encoded by it. Screening the cDNA or genomic library with the selected probe may be conducted using standard procedures as described in Sambrook et al, Molecular Cloning: A Laboratory Manual (New York: Cold Spring Harbor Laboratory Press, 1989). An alternative means to isolate the gene encoding ChrR polypeptide is to use PCR methodology.

The nucleic acid encoding a ChrR polypeptide is inserted into a replicable vector for expression. Many such vectors are available. The vector components generally include, but are not limited to, one or more of the following: an origin of replication, one or more marker genes, an enhancer element, a promoter, and a transcription termination sequence. In some embodiments, for example in the utilization of bacterial delivery agents such as *Salmonella*, the chrR gene is integrated into the host cell chromosome.

ChrR polypeptides may be produced recombinantly not only directly, but also as a fusion polypeptide with a heterologous polypeptide, e.g. a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell.

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors will contain a promoter that is recognized by the host organism and is operably linked to the ChrR coding sequence. Promoters are untranslated sequences located upstream (5') to the start codon of a structural gene (generally within about 100 to 1000 bp) that control the transcription n of particular nucleic acid sequence to which they are operably linked. In bacterial cells, the region controlling overall regulation can be referred to as the operator. Promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known. Both a native ChrR polypeptide promoter sequence and many heterologous promoters may be used to direct expression of a ChrR polypeptide. However, heterologous promoters are preferred, as they generally permit greater transcription and higher yields.

Promoters suitable for use with prokaryotic hosts include the β-lactamase and lactose promoter systems, alkaline phosphatase, a tryptophan (trp) promoter system, hybrid promoters such as the tac promoter, and starvation promoters (Matin, A. (1994) Recombinant DNA Technology II, Annals of New York Academy of Sciences, 722:277-291). However, other known bacterial promoters are also suitable. Such nucleotide sequences have been published, thereby enabling a skilled worker operably to ligate them to a DNA coding sequence. Promoters for use in bacterial systems also will contain a Shine-Dalgarno (S.D.) sequence operably linked to the coding sequence.

Promoter sequences are known for eukaryotes, e.g. for use with viral expression systems. Examples of suitable promoting sequences include promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3° to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter. Small RNAs may be used for enhancing translation.

Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs.

Construction of suitable vectors containing one or more of the above-listed components employs standard ligation techniques. Isolated plasmids or DNA fragments are cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis*, Pseudomonads such as *P. aeruginosa*, and *Streptomyces*. These examples are illustrative rather than limiting.

The term "plasmid" as used herein refers to any nucleic acid encoding an expressible gene and includes linear or circular nucleic acids and double or single stranded nucleic acids. The nucleic acid can be DNA or RNA and may comprise modified nucleotides or ribonucleotides, and may be chemically modified by such means as methylation or the inclusion of protecting groups or cap- or tail structures. Replicating plasmids can be identified using standard assays including the standard replication assay of Ustav and Stenlund (1991).

The present disclosure also provides a host cell transfected with the isolated polynucleotide or vector comprising such a polynucleotide of the present disclosure. The host cell may be a mammalian cell, e.g. a patient cell transfected with a viral vector, or may be a bacterial cell, e.g. an attenuated *S. typhimurium* cell.

Expression vectors of interest include any DNA or RNA vector used in Viral Directed Enzyme Prodrug Therapy (VDEPT) or Gene Directed Enzyme Prodrug Therapy (GDEPT) therapies. Integrating vectors of interest include recombinant retroviral vectors. A recombinant retroviral vector will include DNA of at least a portion of a retroviral genome which portion is capable of infecting the target cells. The term "infection" is used to mean the process by which a virus transfers genetic material to its host or target cell. Preferably, the retrovirus used in the construction of a vector of the disclosure is also rendered replication-defective to remove the effect of viral replication on the target cells. In such cases, the replication-defective viral genome can be packaged by a helper virus in accordance with conventional techniques. Generally, any retrovirus meeting the above criteria of infectivity and capability of functional gene transfer can be employed in the practice of the disclosure. Lentiviral vectors are especially preferred. Suitable retroviral vectors include but are not limited to pLJ, pZip, pWe and pEM, well known to those of skill in the art. Suitable packaging virus lines for replication-defective retroviruses include, for example, ΨCrip, ΨCre, Ψ2 and ΨAm.

Examples of vector systems include vectors based on the Molony murine leukaemia virus (Ram et al., Cancer Research (1993) 53; 83-88; Dalton and Triesman, Cell (1992) 68; 597-612). These vectors contain the murine leukaemia virus (MLV) enhancer cloned upstream at a β-globin minimal promoter. The β-globin 5' untranslated region up to the initiation ATG is supplied to direct efficient translation of the cloned protein. The initiator ATG straddles an NcoI restriction site and thus can be used to clone a protein coding sequence into the vector. This vector further contains a polylinker to facilitate cloning, followed by the β-globin 5' untranslated region and polyadenylation sites. The MLV enhancer is of particular use since it is a strong enhancer and is active in most murine and human cells.

Suitable viral vectors further include those which are based upon a retrovirus. Such vectors are widely available in the art. Huber et al., (Proc. Natl. Acad. Sci. USA (1991) 88, 8039) report the use of amphotropic retroviruses for the transformation of hepatoma, breast, colon or skin cells. Culver et al (Science (1992) 256; 1550-1552) also describe the use of retroviral vectors in GDEPT. Such vectors or vectors derived from such vectors may also be used. Other retroviruses may also be used to make vectors suitable for use in the present disclosure. Such retroviruses include rous sarcoma virus (RSV). The promoters from such viruses may be used in vectors in a manner analogous to that described above for MLV.

Englehardt et al., (*Nature Genetics* (1993) 4:27-34) describes the use of adenovirus based vectors in the delivery of the cystic fibrosis transmembrane conductance product (CFTR) into cells, and such adenovirus based vectors may also be used. Vectors utilizing the adenovirus promoter and other control sequences may be of use in delivering a system according to the disclosure to cells. Adenovirus vectors are well known to those skilled in the art and have been used to deliver genes to numerous cell types; including airway epithelium, skeletal muscle, liver, brain and skin (Hitt et al., 1997; Anderson, 1998).

Another vector is the adeno-associated (MV) vector. MV vectors are well known to those skilled in the art and have been used to stably transduce human T-lymphocytes, fibroblasts, nasal polyp, skeletal muscle, brain, erythroid and haematopoietic stem cells for gene therapy applications (Philip et al., 1994; Russell et al., 1994; Flotte et al., 1993; Walsh et al., 1994; Miller et al., 1994; Emerson, 1996). International Patent Application WO 91/18088 describes specific MV based vectors.

Other episomal vectors include transient non-replicating episomal vectors and self-replicating episomal vectors with functions derived from viral origins of replication such as those from EBV, human papovavirus (BK) and BPV-1. Such integrating and episomal vectors are well known to those skilled in the art and are fully described in the body of literature well known to those skilled in the art. In particular, suitable episomal vectors are described in WO98/07876.

Numerous techniques are known and are useful according to the disclosure for delivering the vectors described herein to cells, including the use of nucleic acid condensing agents, electroporation, complexing with asbestos, polybrene, DEAE cellulose, Dextran, liposomes, cationic liposomes, lipopolyamines, polyornithine, particle bombardment and direct microinjection (reviewed by Kucherlapati and Skoultchi, 1984; Keown et al., 1990; Weir, 1999; Nishikawa and Huang, 2001).

A vector may be delivered to a host cell non-specifically or specifically (i.e., to a designated subset of host cells) via a viral or non-viral means of delivery. Delivery methods of viral origin include viral particle-producing packaging cell lines as transfection recipients for the vector of the present disclosure into which viral packaging signals have been engineered, such as those of adenovirus, herpes viruses and papovaviruses. Non-viral based gene delivery means and methods may also be used in the disclosure and include direct naked nucleic acid injection, nucleic acid condensing peptides and non-peptides, cationic liposomes and encapsulation in liposomes, bacterial cells, and the like.

Certain publications have described the use of exosome compositions and methods of their use: For example, PCT Publication WO 2014/089124 and corresponding US Patent Application Publication US2016/038576 describe a method for evoking an immune response specific for a senescent cell in a subject, wherein the immune response comprises clearance of the senescent cell by the immune system of the subject, said method comprising administering to the subject an immunogenic composition comprising, in part, a senescent cell membrane preparation, a senescent cell organelle preparation, or an exosome.

Exosome Production

Exosome producing cells may be any cell, preferably of mammalian origin, that produces and secretes membrane vesicles of endosomal origin by fusion of late endosomal multivesicular bodies with the plasma membrane. Endosomal producing cells include, for example, dendritic cells, B cells, tumor cells, senescent cells, T cells, and mast cells. In one embodiment, exosome-producing cells are mammalian senescent cells, mammalian T cells, and mammalian dendritic cells, typically murine (useful for preclinical studies) or human. Dendritic cell exosomes are capable of activating T cells and NK cells. In certain embodiments, exosomes may be obtained from any autologous subject-derived cells, heterologous haplotype-matched cells, or heterologous stem cells to reduce or avoid the generation of an immune response in a subject to whom the exosomes are administered. For evoking production of antibody(ies), B cells may be used as exosome producing cells because the resulting exosomes comprise accessory functions and molecules such as MHC Class II molecules that facilitate antibody production. Additionally, B cell exosomes are able to bind follicular dendritic cells, which is a feature of antibody induction. Exosomes from other cells types, such as non-antigen presenting cells, for example, senescent cells, can spread antigens or peptide-loaded MHC complexes to antigen presenting cells for more efficient presentation. Recombinant exosomes comprising recombinant MHC molecules have also been described (See, e.g., WO00/028001, incorporated herein in its entirety). In some embodiments, exosomes originating from one or more cell types may be used.

One or more cell surface receptor membrane-associated antigens or antigenic fragments thereof may be selected for loading of exosome producing cells. If the exosome producing cell is a cancer cell, it is naturally loaded with tumor-cell associated antigens or antigenic fragments thereof. An exosome producing cell may also be modified with specific recombinant tumor cell-associated antigens or antigenic fragments thereof, co-stimulatory molecules, targeting moieties, or loaded with an exogenous antigen (i.e., a helper antigen or carrier protein) to enhance the immune response. A variety of methods known in the art may be used to load antigen presenting cells with antigens, including peptide pulsing (See, e.g., Macatonia et al., 1989, *J. Exp. Med.* 169:1255; Takahashi et al., 1993, *Int. Immunol.* 5:849), antigen pulsing (See, e.g., Inaba et al., 1990, *J. Exp. Med.* 172:631; Hsu et al., 1996, *Nat. Med.* 2:52); placing cells in contact with one or more antigenic protein complexes; placing cells in contact with cells or membranes of cells expressing antigens or antigenic peptides ("direct transfer") (See, e.g., Zou et al., *Cancer Immunol. Immunother.* 15:1); placing cells in contact with membrane vesicles containing antigens or antigenic peptides (e.g., exosomes from senescent cells) (See, e.g., U.S. Pat. No. 6,685,911); placing cells in contact with liposomes containing antigens or antigenic peptides (See, e.g., Nair et al., 1992, *J. Exp. Med.* 175:609); placing cells in contact with polynucleotides encoding antigens or antigenic peptides (optionally incorporated in vectors of plasmid, viral, or chemical type) (See, e.g., Boczkowsky et al., 1996, *J. Exp. Med.* 184:465-472; Bhardwaj et al., 1994, *J. Clin. Invest.* 94:797; Alijagie et al., 1995, *Eur J. Immunol.* 25:3100). Methods of producing, purifying, or using exosomes for therapeutic purposes or as research tools are known in the art and have been described, for example, in U.S. Pat. Nos. 6,685,911; 7,625,573; PCT Publication Nos. WO99/03499; WO00/44389; WO00/028001; and WO97/05900, each of which is incorporated by reference herein in its entirety.

Exosomes produced by the exosome-producing cell may be collected and/or purified using techniques known in the art, such as differential centrifugation, chromatography, etc. (See, e.g., Thery et al., 1999, *Cell Biol.* 147:500-10; Lehmann et al., 2008, *Cancer Res.* 68:7864; U.S. Patent Publication No. 2004/0241176; U.S. Pat. No. 6,899,863; PCT Publication No. WO 2000/44389; each of which is incorporated herein by reference in its entirety). Methods for targeting expression of recombinant polypeptides to exosomes using exosome-specific targeting domains (e.g., C1 and/or C2 domains from the lactadherin protein, also known as "Milk Fat Globule-EGF Factor 8 protein" or MFGE8) have been described in U.S. Pat. No. 7,704,964, to Delacyre, et al. and incorporated by reference herein in its entirety; as well as in Rountree et al., 2011, *Cancer Res.* 71:5235. Exosome producing cells may also be modified such that exosomes include a targeting moiety on the surface. The exosomes may be targeted to a selected tissue or cell type (See, e.g., POT Publication No. WO 2010/119256, incorporated herein in its entirety).

The present disclosure describes directed and loaded EXO-DEPT exosomes decorated with ligands that enable them to specifically target cells or tissues overexpressing a cell surface receptor, for specific delivery of therapeutic molecules (a specific drug, a gene or other active nucleic acid and/or biomolecule such as mRNA, siRNA or miRNA, a polypeptide/protein, an antibiotic, or a small molecule compound), and methods for use of these exosomes in the treatment of cancer or other diseases in which specific extracellular receptors are overexpressed.

This disclosure represents a new approach in the therapeutic regimen termed "Gene-delivered Enzyme Prodrug Therapy (GDEPT)," with the novelty being that mRNA is used (instead of DNA) for gene delivery, and exosomes are used as vehicles for the delivery and activation of a new prodrug. The composition and methods employ a new chimeric protein construct, termed EVHB, consisting of: i) lactadherin leader sequence (LS) for EVHB migration to the exosome surface; ii) high affinity anti-HER2 scFv antibody to target the HER2 receptor; iii) lactadherin 01-02 domains, which bind to exosomes by interacting with their surface phosphatidylserine; and iv) His-tag, for EVHB purification. HEK293 cells transfected with the plasmid encoding this protein generate exosomes that express EVHB on their surface and have the capability of specifically targeting HER2-positive receptor, cells, and tumors (termed, "targeted" exosomes). These exosomes have also been loaded with exogenous mRNA, using the 'zipcode' technology that promotes mRNA entry into exosomes and a commercially available plasmid. The directed and loaded exosomes (called the "EX©-DEPT" exosomes) specifically deliver the mRNA to HER2-positive cells and tumors in mice. The mRNA encodes humanized and improved form of a bacterial enzyme, called HChrR6. This enzyme can convert a harmless prodrug, 6-chloro-9-nitro-5-oxo-5H-benzo-(a)-phenoxazine (CNOB), into the highly toxic drug, 9-p amino-6-chloro-5H-benzo'a"phenoxazine-5-one (MCHB). MCHB is strongly fluorescent and can be quantitated by its fluorescence intensity; it can also be visualized in living mice. As the mRNA is delivered specifically to the tumors, HChrR6 is generated specifically inside them. Consequently, the toxic drug, MCHB, is confined largely to the tumors attaining a high concentration inside them. Advantages of these innovations include the effective killing of cancer cells, avoidance of drug resistance, and prevention of damage to normal tissues. HChrR6 can also activate the prodrug CB1954, which has already been approved for clinical trials; this will facilitate approval of the current invention for clinical trials. Additionally, combined therapy with the two prodrugs can enhance the effectiveness of the treatment. The composition and methods described are generic and the anti-HER2 scFv in the EVHB construct can be easily replaced by another scFv (or other moieties) capable of targeting a different receptor; and the exosomes/EVs can be loaded with another mRNA, biomolecule and/or drug. Thus, the approach can be used for therapy of any disease in which a receptor is overexpressed. Examples of other receptors overexpressed in cancers are PSMA, bombasin, folate, transferrin, and sigma; many other diseases also overexpress specific receptors.

One use of the presently disclosed compositions and methods is to specifically deliver drugs or other beneficial biomolecules to cells, tumors and tissues, for prevention, treatment, or amelioration of cancer and/or other diseases in which a receptor is overexpressed.

In some embodiments, the disclosure concerns HER2-positive breast cancer (a serious disease with poor prognosis), in which the HER2 receptor is overexpressed. Confinement of the drug or therapeutic agent primarily or exclusively to the cancer location will eliminate the severe side effects that accompany current chemotherapeutic approaches. While the particular examples represent the treatment or amelioration of HER2-positive breast cancer, the approach envisaged is generally applicable to other cancers in which an extracellular receptor is overexpressed. As such, the compositions and methods described herein can be employed to treat other cancers or hyperproliferative diseases, disorders or conditions, such as those overexpressing PSMA, bombasin, folate, transferrin, and/or sigma receptors. In many other diseases as well, receptors are overexpressed; these too can benefit from specific delivery of a drug and/or biomolecule that the disclosed disclosure makes possible.

The disclosure employs exosomes, also called extracellular vesicles (EVs), modified for messenger RNA-based, instead of DNA-based gene delivery; the advantages of using exosomes and mRNA for gene delivery are mentioned below. "EXO-DEPT" exosomes were generated that are capable of specifically targeting the HER2 receptor and delivering to HER2-positive cells and tumors an mRNA that confers on the cells or tumors the capability to convert a harmless prodrug to a highly toxic drug. Treatment with the EXO-DEPT exosomes (but not by unmodified exosomes) and a prodrug resulted in complete arrest of the growth of implanted orthotopic human HER2-positive tumors in nude mice. This strongly indicates that the delivery of the therapy was confined to the tumor.

Technical Description:

Herein described is the specific targeting of the prodrug/enzyme (CNOB/HChrR6) regimen. HChrR6 is an improved bacterial enzyme that converts CNOB into the cytotoxic drug MCHB. The aim is to develop a new treatment for HER2-positive human breast cancer, a serious disease, with minimal off-target toxicity. Extracellular vesicles (EVs) were used for HchrR6 gene delivery, as they may cause minimal immune rejection; and mRNA could be superior to DNA for this purpose. To confine HChrR6 generation and CNOB activation to the cancer, the EVHB chimeric protein, containing high affinity anti-HER2 (ML39) scFv antibody and capable of latching on to EV surface, was constructed. Cells transfected with EVHB-encoding plasmid, generated EVs displaying this protein, which was purified. Transfection of a separate batch of cells with the new plasmid, XPort/HChrR6, generated EVs containing HChrR6 mRNA; incubation with pure EVHB enabled these ("EXO-DEPT" EVs) to target the HER2 receptor. EXO-DEPT EV treatment specifically enabled HER2-overexpressing BT474 cells to convert CNOB into MCHB in actinomycin D independent manner, showing successful and specific delivery of HChrR6 mRNA. EXO-DEPT EVs, but not of unmodified EVs, plus CNOB treatment caused near-complete growth-arrest of orthotopic BT474 xenografts in vivo, demonstrating for the first time EV-mediated delivery of functional exogenous mRNA to tumors. EXO-DEPT EVs may be generated from patient's own dendritic cells to evade immune rejection, and without plasmids and their potentially harmful genetic material, raising the prospect of clinical use of this regimen. This approach can be employed to treat any disease overexpressing a specific marker.

Exosomes are small lipid bilayer vesicles generated by nearly all body cells and serve as means of intracellular communication. This disclosure reports a method to decorate the surface of exosomes with ligands that enable them to specifically target the HER2 receptor. A new chimeric protein, EVHB, has been constructed. It consists of i) lactadherin leader sequence (LS) for EVHB migration to the exosome surface; ii) high affinity anti-HER2 scFv antibody to target the HER2 receptor; iii) lactadherin C1-C2 domains, which bind to exosomes by interacting with their surface phosphatidylserine; and iv) His-tag, for EVHB in pure state. Immortalized human kidney (HEK293) cells transfected with the plasmid encoding this protein generate exosomes that express EVHB on their surface and have the capability of specifically targeting HER2-positive receptor, cells, and tumors (termed, "targeted" exosomes). EVHB was eluted from these exosomes and purified. Incubation of the exosomes with purified EVHB increases their HER2 receptor targeting capability.

Also developed is a new method for loading these exosomes with exogenous mRNA (never before accomplished), using the 'zipcode' technology that promotes mRNA entry into exosomes, and a commercially available plasmid (the resulting exosomes are referred to as "loaded" exosomes). The directed and loaded exosomes (called the "EXO-DEPT" exosomes) specifically deliver the mRNA to HER2-positive cells and tumors in mice. The mRNA encodes a humanized and improved form of a bacterial enzyme, called HChrR6. This enzyme can convert a harmless prodrug, 6-chloro-9-nitro-5-oxo-5H-benzo-(a)-phenoxazine (CNOB), into the highly toxic drug, 9-p amino-6-chloro-5H-benzo-'a"phenoxazine-5-one (MCHB). MCHB is strongly fluorescent and can be quantitated by its fluorescence intensity; it can also be visualized in living mice. As the mRNA is delivered specifically to the tumors, HChrR6 is generated specifically inside them. Consequently, the toxic drug, MCHB, is confined largely to the tumors attaining a high concentration inside them. This promotes effective killing of the cancer, avoidance of drug resistance, and prevention of damage to normal tissues. HChrR6 can also activate the prodrug CB1954, currently in clinical trials; this facilitates testing of the present invention in clinical trials.

Furthermore, combined therapy with the two prodrugs can enhance the effectiveness of the treatment. This disclosure represents a new approach in the therapeutic regimen termed "Gene-delivered Enzyme Prodrug Therapy (GDEPT), wherein mRNA is delivered and exosomes are used as vehicles for this delivery and activation of a prodrug.

Advantages of these innovations are described below. The anti-HER2 scFv in the EVHB construct can be easily replaced by another scFv (or other targeting moieties) capable of targeting a different receptor; and the EVs can be loaded by another mRNA, biomolecule and/or drug. Thus, the technology disclosed here is generic for therapy of any disease in which a receptor is overexpressed and that can benefit by such specific delivery. Examples of other receptors overexpressed in cancers are PSMA, bombasin, folate, transferrin, and sigma; in addition to cancer, many other diseases also overexpress specific receptors.

Applications:

The disclosure provides for the treatment of any disease, in which a receptor is overexpressed, without generalized, painful, and dangerous side effects. Examples of receptors overexpressed in different cancers are given above; many other diseases also overexpress specific receptors. These too can benefit by specific delivery of a specific drug, gene and/or biomolecule (mRNA, siRNA or miRNA, a polypeptide/protein), an antibiotic, or a small molecule compound, etc.

In some embodiments, the present disclosure provides compositions and methods of making exosomes directed to HER2-positive cancer. As stated, the disclosure permits using the same protocols for making exosomes directed to other indications in which a receptor is overexpressed and that can benefit by specific delivery of a biomolecule(s)/drug(s).

In some embodiments, the present disclosure provides compositions and methods of making exosomes that can deliver exogenous functional mRNA into recipient cells, and this in a targeted manner. This is the first time that functional mRNA, not indigenous to exosomes, has been successfully delivered to recipient cells; and to a beneficial therapeutic end. As stated, EXU DEPT/prodrug joint treatment arrested the growth of implanted xenografts in mice.

In some embodiments, the present disclosure provides compositions and methods for a new form of GDEPT employing exosomes and mRNA that can activate not only CNOB but other reductive prodrugs as well. The present disclosure provides for delivery of a biomolecule introduced into the exosomes specifically to a target, avoiding the deleterious side effects that accompany, for example, the use of conventional chemotherapy.

HChrR6 mRNA in tumors and other body tissues was quantified by qRT-PCR. MCHB fluorescence was measured and used to quantify the amount of drug delivered. The results indicate that HChrR6 mRNA delivery and MCHB generation capability are restricted to the tumor location.

While tumor growth was arrested, the tumors were not eliminated. Thus, the EXO-DEPT/CNOB regimen is being further improved by, for example, increasing the loading of HChrR6 mRNA into the EVs, and optimizing the dosage regimen of EXO-DEPT and CNOB. By increasing the amount of mRNA introduced into the exosomes, the number of exosomes needed for effective therapy is decreased, and the frequency of treatment is minimized; both of these serve to reduce any potential risk arising from the introduction of the native content of exosomes to diseased tissues or tumors.

In addition, immuno-competent mice may be used to combine EXO-DEPT/prodrug and immune-based antitumor effectors. The treatment approach described herein is also effective with the prodrug, CB1954, thus, the efficacy of combined EXO-DEPT/CNOB/CB1954 can also be tested.

In addition to EXO-DEPT exosomes derived from HEK293 cells, EVs can be derived from mesenchymal stem cells or patient's own dendritic cells. This minimizes concerns about adverse immune reactions.

In addition to using DNA-based plasmids for loading mRNA into EXO-DEPT exosomes, mRNA formulations have been efficiently loaded. Using mRNA formulations avoids the possibility of introduction of potentially harmful foreign genetic material into patients, and immune rejection.

The exosome preparation described herein consists of two types of vesicles. One of these may be more effective than the other for EXO-DEPT function. Optimization and further isolation of more effective exosome-mediated delivery component(s) can increase the treatment efficacy.

The patents, patent applications and publications discussed herein are provided solely for their disclosure prior to the filing date of the present application, and are incorporated by reference herein in their entirety. Nothing disclosed herein is to be construed as an admission that the present disclosure is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Materials and Methods

Cell lines, culture and cell viability determination. MCF7, MCF7/ErbB2, BT474, BT474/HER-Res, SKBR3, HEK293, and 293FT cells were used. Cells were cultured in DMEM medium (Thermo Fisher, Carlsbad, Calif.) with 10% fetal bovine serum (FBS) and maintained in a moisturized incubator at 37° C. with 5% $CO_2$. Plasmid p6mLSC1C2, used here, was originally generated by Delcayre and co-workers; it encodes the mouse lactadherin C1-C2 domains that bind to the EV surface, and its leader sequence. Plasmid pACgp67B-HER2m, containing the anti-HER2 scFv (ML39) antibody DNA sequence, was supplied by Addgene (Cambridge, Mass.); ML39 targets the extracellular domain of HER2 receptor. Cell viability was determined by MTT assay (Roche, Mannheim, Germany).

EV preparation. $5\times10^6$ cells in 10 mL DMEM, supplemented with 10% EV-depleted FBS (referred to from hereon as 'DMEM-EDFBS') were plated in a 100 mm dish, and incubated for 4 days. The conditioned medium (containing the EVs) was centrifuged at 600×g followed by 2000×g (30 minutes each) to remove cells and apoptotic bodies, respectively. EVs present in the resulting supernatant were isolated by ultra-centrifugation (100,000×g; 1 hour; 15 minutes). Pellets were suspended in PBS and the EVs were quantified and characterized by protein assay (DC kit, BioRad, Hercules, Calif.) and NanoSight analysis (NanoSight NS300; Melvin Instruments, Melvin, UK).

HER2-targeting chimeric protein, LS-ML39-C1-C2-His (EVHB), preparation. To make this protein, the cDNA sequence of the anti-HER2 scFv antibody, ML39 (See FIG. 5), contained in the pACgp67B-HER2m, was inserted into the p6mLSC1C2 plasmid, using the BsmB1 double restriction sites to construct pEVC1C2HER; the insertion was confirmed by sequencing. $5\times10^6$ HEK293 cells were plated in a 100 mm dish containing 10 mL of DMEM-EDFBS and incubated overnight in a $CO_2$ incubator (37° C.). They were transfected with pEVC1C2HER (7.2 μg) followed by polyethylenimine (PEI) polymer addition and four-day incubation. EVs generated by the transfected cells, which displayed EVHB, were isolated. (EVHB displaying EVs are termed “directed” EVs; those from non-transfected cells, not displaying this protein, are referred to as “naïve”). Directed EVs were also made by incubating naïve EVs with pure EVHB ($2\times10^7$ EVs; 1 μg protein; 15 minute incubation; room temperature).

EVHB was purified as before by dissolving EVHB-displaying EVs in MLBII solution (50 mM NaPO4 pH8/300 mM NaCl/10 mM Imidazole/0.5° 70 Tween20), followed by incubation in equal volume of Ni-NTA resin for 2 hours with mild agitation. All purification steps were done at 4° C. Samples were transferred to a resin-containing column; after the resin settled, it was washed in 5 volumes of MWBI (50 mM NaPO4 pH8/300 mM NaCl/20 mM imidazole/0.05% Tween20), and then in 10 volumes of MWBII (50 mM NaPO4 pH8/300 mM NaCl/20 mM imidazole). The resin-bound protein was eluted in 10 volumes of MEBII (50 mM NaPO4, pH 8/300 mM NaCl/250 mM imidazole), and was concentrated (Pierce protein concentrator; Thermo Fischer). Buffer exchange to PBS was accomplished using Zebra spin desalting columns (Thermo Fischer). Following further concentration using ultra-centrifugal filters (Amicon, Billerica, Mass.), the protein was quantified by DC assay kit (BioRad), using BSA standards (Sigma-Aldrich, St. Louis, Mo.). Its 3-dimensional structure was constructed using Phyre2 (Protein Homology/analogy Recognition Engine V2.0) in intensive mode, followed by analysis using UCSF Chimera software (UCSF Resource for Biocomputing, Visualization and Informatics) to identify the functional domains and their orientations.

Enzyme-linked immunosorbent assay (ELISA). HER2 extracellular domain (ECD) (ACRO Biosystems; Newark, Del.) was dissolved in carbonate buffer (pH 9.6) to a final concentration of 5 μg/mL. All procedures were performed on a shaker with mild agitation. To coat the wells (in a 96-well plate) with ECD, 100 μL of the solution were added to each well and the plate was incubated at 4° C. overnight. The wells were washed three times with washing buffer (PBS with 0.05% Tween20), and treated with blocking buffer (PBS with 0.5% BSA) at room temperature (1 hour). After the addition of EVs ($2\times10^7$ per well) and incubation at room temperature (2 hours), the wells were rinsed three times with washing buffer. Anti-CD63 antibody (BD Pharmigen, San Jose, Calif.; 5 μg/mL in 100 μL of blocking buffer) was then added, followed by incubation at room temperature (1 hour). The wells were washed three times with washing buffer, followed by blocking buffer supplemented with 100 L of HRP goat anti-mouse IgG (diluted 1:5000) and incubation at room temperature (1 hour). After three washes in washing buffer, 100 μL TMB (Sigma-Aldrich) was added to each well (30 minute incubation). The HRP enzymatic reaction was stopped by 1N HCL (100 μL/well). A450 minus the background absorbance ($A_{620}$) indicated the intensity of the EV binding to the HER2 receptor.

Determination of EV binding to cells by microscopy and flow cytometry. Binding of directed EVs [labeled for visualization with CFSE (Thermo Fischer)] to (essentially) HER2-negative (MCF7; 4.7 ng HER2 receptor/mg) and positive (BT474; 530 ng HER2 receptor/mg) cells was compared. $3\times10^4$ cells per well (n=3) were seeded in a black 96-well plate with transparent bottoms (Thermo Fisher) and exposed to naïve unlabeled EVs in DMEM/10% FBS overnight to block nonspecific binding. Directed or naïve CFSE-labeled EVs were then added to separate groups of wells and incubated in DMEM/EDFBS for 6 hours (37° C.) followed by washing in the same medium to remove unbound EVs, and addition of fresh medium (100 μL). Green fluorescence (GFP filter) and phase contrast images were taken (20× magnification; EVOS™ FL Cell Imaging System, Thermo Fisher).

Cell binding was analyzed also by flow cytometry. BT474 cells tended to form clumps and proved unsuitable for cell sorting. Thus, HER2-positive SKBR3 cells (HER2 content, 913 ng/mg) were used; MCF7 cells were again used as control. The EVs were labeled with PKH26 dye (Sigma-Aldrich). EVs were obtained as above and suspended in 1 mL Diluent C (Sigma-Aldrich). PKH26 dye (4 μL) was added to the suspension and incubated at room temperature (5 minutes). Labeling was stopped by adding 0.5 mL of PBS-2% BSA. The labeled EVs were pelleted as above, and re-suspended in 1 mL fresh PBS, followed by removal of any remaining unbound dye using Pierce buffer exchange column (Thermo Fisher). SKBR3 cells were seeded in 6-well plates ($1.2\times10^6$/well) in DMEM with 10% FBS, and incubated overnight. The medium was then replaced with DMEM/EDFBS containing $1.6\times10^9$ directed EVs to the wells and incubated (37° C.; 4 hours). Cells were washed with ice-cold PBS; 0.2 mL/well of cell detaching solution in PBS (Thermo Fisher) was added to dislodge the cells, which were mixed with 1 mL DMEM 10% FBS. Cells were transferred to centrifuge tubes, pelleted by centrifugation (900×g; 4° C.; 5 minutes), rinsed in 1 mL FACS buffer (PBS with 1% BSA and 0.1% $NaN_3$), washed with 1 mL of acid buffer (0.5M NaCl; 0.2M acetic acid, pH 3.0) to remove non-internalized EVs, followed by treatment with Flow Cytometry Fixation Buffer (R&D Systems, Minneapolis, Minn.) (4° C.; overnight). The fixed cells were pelleted by centrifugation (900×g; 4° C.; 5 minutes), resuspended in 1 mL of FACS buffer, and filtered through a 40 μm cell strainer (BD Biosciences). Aliquots were analyzed by the Scanford FACS analyzer (Stanford FACS facility, Stanford, Calif.; excitation, 488 nm; emission, 590/20 nm).

Loading EVs with HChrR6 mRNA. The electroporation protocol of Wood and coworkers was used. HChrR6 mRNA (1 μg) was suspended with the EVs in Cytomix electroporation buffer (BioRad) and electroporated at 100 to 400V (125 μF). EVs were then isolated with latex beads (Thermo Fisher), and the amount of HChrR6 transcript was analyzed by qRT-PCR. As described below, this approach having proved inadequate, a novel method was developed to load EVs with HChrR6 mRNA that involved construction of a new plasmid pXPort/HChrR6, utilizing SBI XPort plasmid (SBI, Palo Alto, Calif.). To prepare EVs loaded with HChrR6 mRNA, $5\times10^6$ 293 FT cells were transfected with pXPort/HChrR6 plasmid (7.2 μg/100 mm cell culture plate), followed by the addition of PEI (2.5 plasmid weight), and incubation in a $CO_2$ incubator (37° C.; 4 days). 293FT strain contains SV40 large T antigen; this promotes high level transgene expression from vectors containing the SV40 promotor. The EVs were isolated by differential centrifugation as above. (EVs containing HChrR6 mRNA are termed “loaded” EVs.)

RNA extraction from EVs and cells and quantitative RT-PCR. RNA was extracted using RNeasy mini kit (QIAGEN, Germany), and quantified by NanoDrop 1000 Spectrophotometer (Thermo Fisher, Wilmington, Del.). cDNA was synthesized from RNA of EVs and cells (0.1 and 1 μg, respectively), using M-MuLV reverse transcriptase (Taq®

RT-PCR kit, New England Biolabs (NEB), Ipswich, Mass.). To remove RNA, the cDNA was treated with RNase H (NEB). Quantitative PCR was performed using Maxima SYBR Green/ROX qPCR Master Mix kit (Thermo Fisher) and 7500/7500 Fast Real-Time PCR System (Applied Biosystems, East Lyme, Conn.). GAPDH mRNA was used as endogenous control. The following primers were used:

```
HChrR6 Forward    5'-GCAGATCCTCGTGTTCCTGGA-3',

HChrR6 Reverse    5'-CCTGGTCAATCACTTCTCCGTTCT-3',

GAPDH Forward     5'-GGGTGTGAACCATGAGAAGT-3'
and

GAPDH Reverse     5'-GGCATGGACTGTGGTCATGA-3'.
```

The EV-internalized mRNA content was estimated using a standard curve from which the HChrR6 mRNA copy number was calculated, using the following formula: [X(ng)×$6.0221\times10^{23}$(molecules/mole)]/[N×330(g/mole)×$10^9$(ng/g)], where X is the amount of internalized mRNA, N is its length, and 330 g is the average molecular weight of individual nucleotides (Rhode Island Genomics and Sequencing Center, Kingston, R.I.).

In vitro assays for EXO-DEPT EV functionality. BT474 cells suspended in 100 μL DMEM-EDFBS were seeded ($3\times10^4$ per well) in a 96-well plate, and incubated at 37° C. for 4 hours to allow attachment. EVs ($8\times10^8$) were added to each well, followed by overnight incubation. For treatment with actinomycin D (10 μg/mL) or cycloheximide (1 μM), cells were pre-incubated in the same medium supplemented with either of these inhibitors (3 hours). The medium was then replaced with 100 μL of phenol red-free DMEM/10% FBS supplemented with 15 μM CNOB. After 24 hour incubation, functional activity of the EV-delivered HChrR6 mRNA in target cells was determined by measuring MCHB fluorescence (excitation at 570 nm; emission at 620 nm), using a fluorescence plate reader (SpectraMax, Molecular Devices, Sunnyvale, Calif.).

In vivo assays for EXO-DEPT EV functionality. All animal experiments were performed in accordance with protocols approved by Stanford University Institutional Animal Care and Use Committee. Number of mice required for this study was determined by power analysis using the G*Power 3.1.5 power calculator (Universitat Dusseldorf) for F-tests of one-way ANOVA by setting Type I error at 5% (alpha=0.05); power was kept at 0.8, and the number of treatment groups=5. The effect size f was calculated as 0.707. This number was then used to determine total sample size of 30 with 6 mice per treatment group (n=6). Six to seven weeks old female BALB/C athymic nude mice (nu/nu; Charles River Laboratories) were implanted subcutaneously with 0.5 mg (60-day release), 1713-estradiol pellets (Innovative Research of America; Sarasota, Fla.) on the upper dorsal side between the ear and shoulder to support growth of BT474 xenografts, which, in addition to HER2 overexpression, express also the estrogen receptor; a trocar needle was used. On the following day, $10^7$ BT474 cells suspended in 100 μL of PBS-Matrigel (1:1; BD Biosciences, San Jose, Calif.) were subcutaneously injected into mammary fat pad number 9. Tumor size was monitored by caliper at two-day intervals, and tumor volume was calculated using the formula: tumor width$^2$×its length/2. After the tumors reached a volume of >150 $mm^3$, mice were randomly assigned into groups. EVs were pre-loaded with HChrR6 mRNA. $2\times10^9$ EVs in 100 μL PBS were injected intraperitoneally per mouse per dose. Control mice received an equal amount of PBS. The administration schedule, based on previous PK/PD studies of the CNOB/hChrR6 regimen, is provided below.

Data and statistical analysis. All data were calculated and analyzed by the GraphPad Prism software (GraphPad Software Inc., La Jolla, Calif.). Statistics were determined using Student's t-test; p values of less than 0.05 were considered significant. Further details of in vivo experiment data analysis are presented in Tables 1-4, presented hereinbelow.

CNOB/ChrR6 treatment is effective in vitro against HER2-positive human breast cancer cells. The CNOB/ChrR6 prodrug approach was found to be effective in killing several different kinds of cancer cells, but this approach had not been tested on HER2-positive breast cancer cells. FIG. 1 shows that the regimen is highly effective ($p<0.001$) in killing human breast cancer cells regardless of whether they are essentially HER2-negative (MCF7, 4.7 ng HER2 receptor/mg) or strongly positive (BT474, 530 ng HER2 receptor/mg), including a HER2-positive Trastuzumab resistant cell line (BT474/HER-Res). (MCF7 cells, as used herein, are referred to as HER2-negative.)

FIG. 1: Residual survival of cells after CNOB (15 μM) and ChrR6 (50 μg/mL) treatment (24 hours) in vitro. Cell viability was determined by MTT assay. Data are presented as percent survival compared to untreated controls of the corresponding cells. MCF7 cells express low and BT474 cells high levels of the HER2 ligand (see text). HER2-overexpressing counterpart of MCF7 cells ("MCF7/ErbB2") were included, as were Trastuzumab-resistant BT474 cells ("BT474/HER2-Res") ***$p<0.001$ as compared to untreated control of the corresponding cell line.

FIGS. 2A-2D: 2A shows a schematic representation of the HER2 receptor targeting ML39 chimeric protein (EVHB). From left to right, starting at 5' end, "LS" is the Mfge8 leader sequence for export across the membrane; "ML39 scFv" is the high affinity (Kd=10-9M) HER2-targeting moiety; "Lactadherin C1C2" domains are for EV surface binding; "His" is a His-tag for purification. 2B shows a NanoSight analysis of the EVs, where concentration of particles/ml is plotted vs. size (nm). 2C shows Western blots of extracted protein from EVs or whole cells of HEK293 cells transfected with pEVC1C2HER plasmid, or the empty plasmid (p6mLSC1C2; control); the 68 kDa band is seen only in the transfected cells and EVs generated from them. 2D shows the predicted protein structure of EVHB. At the top, lighter ribbon is the ML39 scFv antibody; in the middle is the leader sequence; at the bottom are the C1 and C2 domains.

FIGS. 3A-3D: 3A. ELISA detection of HER2 receptor binding activity of directed EVs (displaying EVHB) obtained from pEVC1C2HER plasmid-transfected HEK293 cells and of naïve EVs obtained from non-transfected HEK293 cells incubated with pure EVHB; the latter show greater binding capability (see text for further details). No signal resulted when naïve EVs (isolated from non-transfected HEK293 cells not incubated with EVHB) or PBS. Bars represent average value±SD (n=3). * $p<0.001$ as determined by t-test between groups as indicated. 3B. Schematic representation of EVHB display by EVs from HEK 293 cells (upper left cell containing organelles). The left panel labeled "Transfection" shows cells transfected with pEVC1C2HER plasmid, and EVs obtained from them, with an enlarged EV showing the membrane bilayer. The right panel labeled "Reconstitution" shows non-transfected cells after incubation with pure EVHB which is inserted into the membrane bilayer. 3C. Representative fluorescent and phase contrast images of corresponding regions showing the CFSE-labeled directed EV binding to BT474 cells and not to MCF7 cells. 3D**. Directed EV binding to cells as determined by flow cytometry. Left panel: fluorescence shift caused by the indicated cell types (or mixture; fluorescence intensity peaks for each cell type are indicated with an arrow). The shift due to SKBR3 cells is arbitrarily assigned a value of 1 (see Results). Right panel: Quantification of the relative shifts based on the data of the left panel.

FIGS. 4A-4G: 4A. The design of XPort/HChrR6 plasmid showing key features involved in mRNA packaging into EVs; see text for details. 4B. ciPCR results showing successful loading of EVs with HChrR6 mRNA. Endogenous EV miR-16 level was determined as control [the Ct value of mRNA corresponds to $2\times10^{-4}$ copy/EV]. 4C. In vitro effectiveness of EXU-DEPT EVs. BT474 cells ($3\times10^4$) treated with $8\times10^8$ EXU-DEPT EVs generated MCHB fluorescence upon CNOB treatment, naïve EVs alone, or loaded but non-directed EVs (not displaying EVHB) show only background fluorescence upon CNOB treatment. 4D. MCHB fluorescence normalized to cell viability. BT474 cells treated with EXU-DEPT EVs and CNOB generate MCHB fluorescence, and this was not affected by the presence of actinomycin D, but is eliminated in the presence of cyclohexamide (CHX). See text for further details. Bars represent average value±SD (n=3). * $p<0.001$,  $p<0.01$ as compared between groups as indicated. 4E. Administration schedule of EVs and CNOB for in vivo test of the effect of EXU-DEPT EVs on orthotopically implanted BT474 tumors in nu/nu mice; each administration consisted of the indicated EV and CNOB amounts; the number of EVs used delivered $4\times10^5$ copies of the HChrR6 mRNA per injection. 4F. Plot of average tumor volume recorded twice a week for the indicated treatment groups. 4G. Rate of tumor growth calculated from slopes of linear regression shown in Box and Whisker plot for each treatment group. Statistical analysis of linear regression slopes between groups was performed by two-samples, two-sided t-test, and confirmed by Tukey's honest significance difference test as post-hoc. * $p<0.001$,  $p<0.01$, * $p<0.05$ as compared between groups as indicated. Further statistical analysis is provided in Tables 1-4 presented herein.

Figure 5:
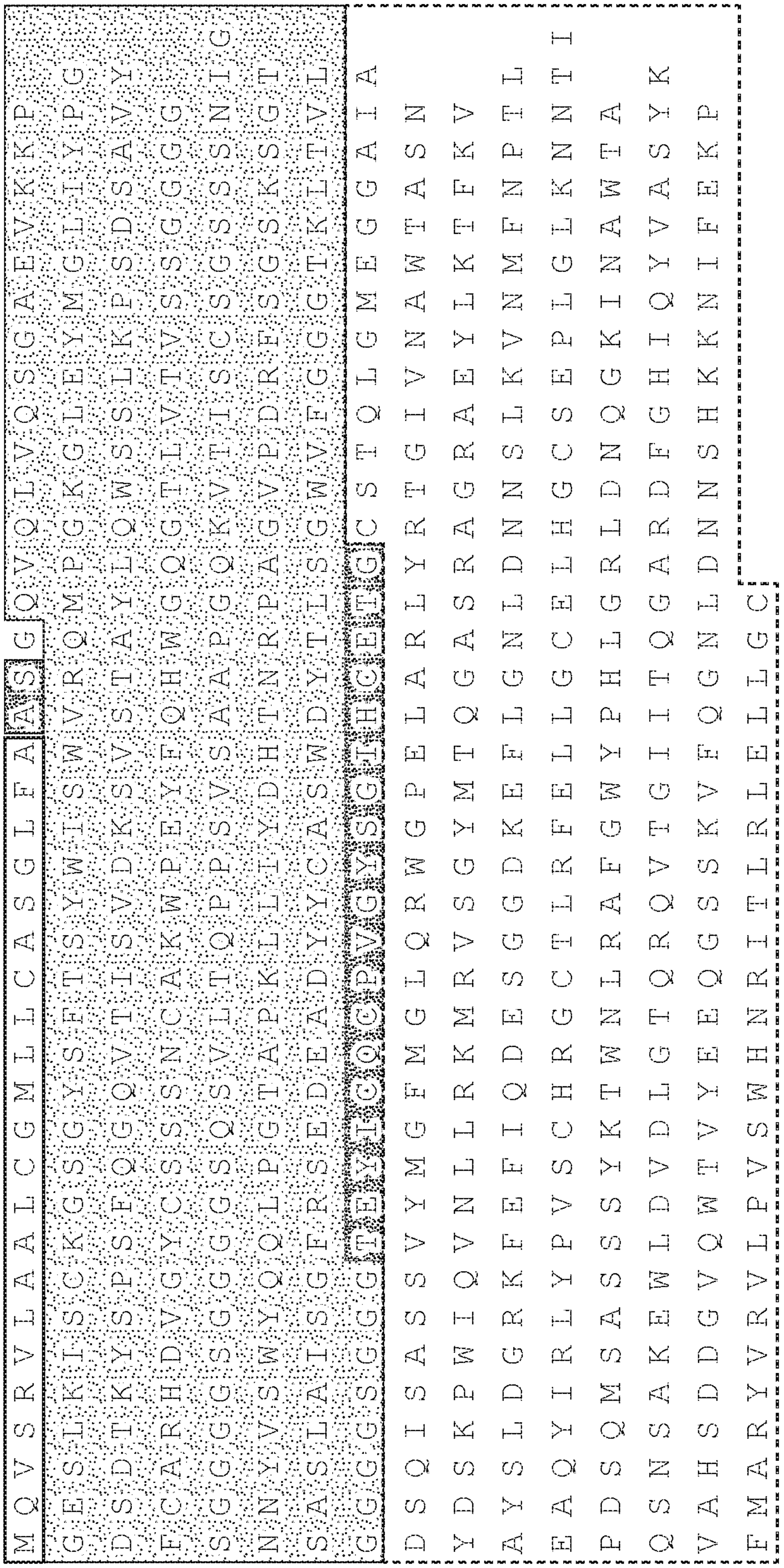
FIG. 5 shows the EVHB chimeric protein sequence (herein identified and SEQ ID NO. 2), having 622 amino acids and a calculated molecular weight of 67,353 (approximately 68 kDa). Sequence regions of different highlighted colors represent functional domains. Darkest grey (■)=Leader sequence; Lightest grey (■)=ML39; (■)=linker domain; Dark medium grey (■)=C1C2 domains.

FIG. 5: EVHB chimeric protein sequence (SEQ ID NO. 2). The chimeric protein consists of 622 amino acids with calculated molecular weight of 67,353 (approximately 68 kDa). Sequence regions of different highlighted colors represent functional domains. Darkest grey (■)=Leader sequence; Lightest grey (▨)=ML39; Light medium grey (▨)=linker domain; Dark medium grey (▨)=C1C2 domains.

Figure 2A:
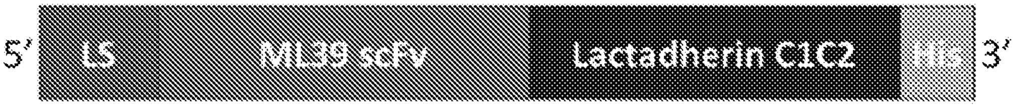
FIGS. 2A-2D.
Figure 2B:
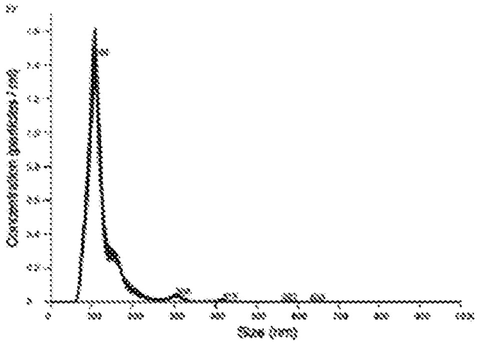
Figure 2C:
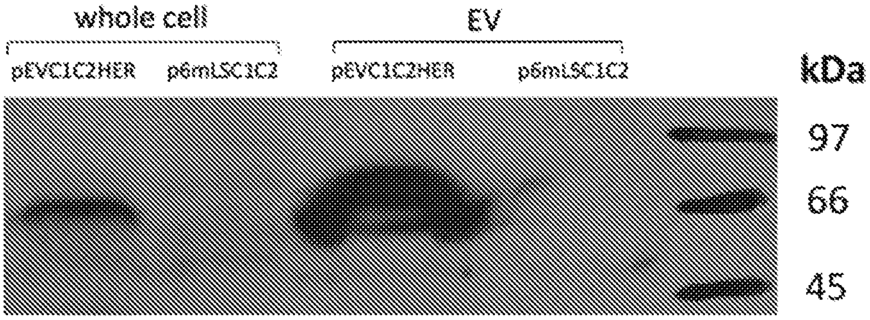
Figure 2D:
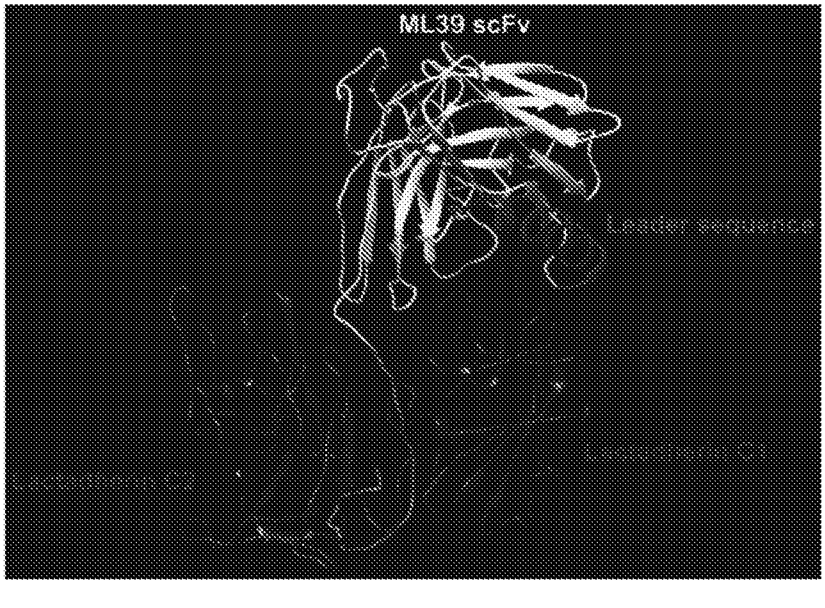

HER2 targeting EVs. To confer on EVs the capability to target HER2 receptor, the plasmid pEVC1C2HER was constructed. It encodes a chimeric protein, termed EVHB (See FIG. 2A and FIG. 5), consisting of: i) lactadherin leader sequence (LS) for EVHB migration to the EV surface; ii) high affinity anti-HER2 scFv antibody (ML39; [K(d)=$10^{-9}$M; to target the HER2 receptor, connected through a flexible linker to iii) lactadherin 01-02 domains, which bind to EVs by interacting with their surface phosphatidylserine; and iv) His-tag, for purification. FIG. 5 shows the amino acid composition of EVHB, indicating a calculated molecular weight of 68 kDa. Immortalized human kidney embryonic (HEK293) cells were transfected with pEVC1C2HER, and the cell-released EVs were isolated; they presented a uniform peak in NanoSight analysis (average size, ca. 30-100 nm; FIG. 2B). EVHB was purified both from the EV and cell lysates. Equal protein amounts were analyzed by Western blotting; the expected 68 kDa band was seen, which was more intense for the EV fraction (FIG. 2C); the band was not found in extracts of non-transfected cells or their EVs. The predicted three-dimensional structure of EVHB (FIG. 2D) is further elucidated in a video, showing rotation of the structure along two axes. It is evident that ML39 with its heavy and light chains is exposed outward, is joined to LS, and C1 and C2 domains are below it, orientated in opposite directions. This is consistent with EVHB binding to the EVs to display ML39, thereby enabling them to target the HER2 receptor.

Figures 3A, 3B, 3C:
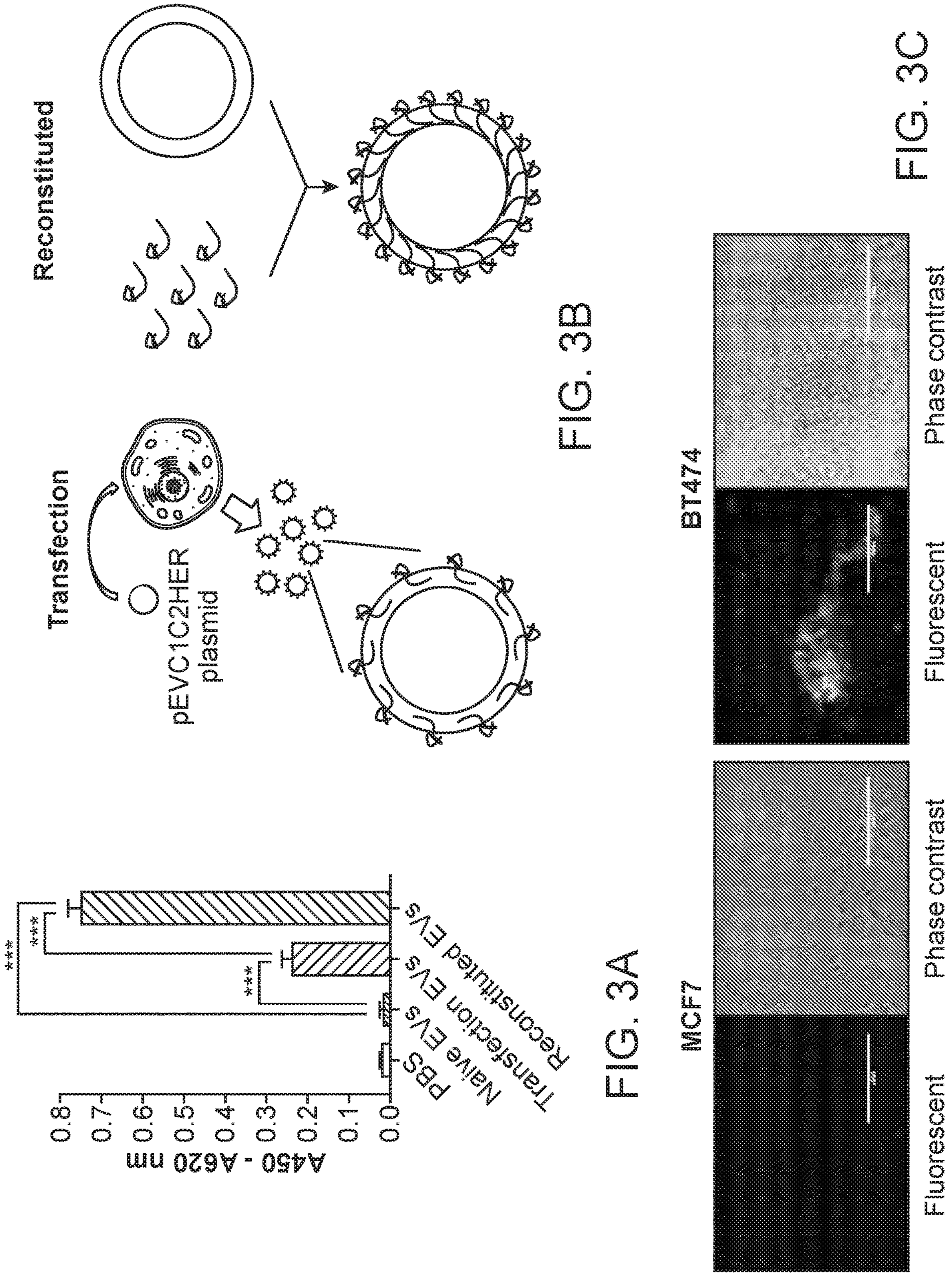
FIGS. 3A-3D.

Two methods to generate directed EVs were tested: one, by obtaining them from pEVC1C2HER-transfected HEK293 cells, and the other, by first generating naïve EVs from non-transfected HEK293 cells and incubating them with pure EVHB. ELISA tests showed that the latter possessed 10-fold greater binding capability to the HER2 receptor as compared to the former ('Reconstitution' vs. 'Transfection' EVs; FIG. 3A). Without being bound by theory, this may be because the transfected cells transported less EVHB to the EV surface than the locations available for its binding, and that greater binding saturation occurs when EVHB is externally added. This is illustrated in FIG. 3B (Transfection' vs. 'Reconstitution'). As all subsequent work employed such 'reconstituted' EVs, the term 'directed' will denote these EVs.

The relative binding of directed EVs to HER2-overexpressing BT474 and HER2-negative MCF7 cells was compared. The EVs, labeled with the fluorescent dye CFSE, were added to the cells. Fluorescent and phase contrast microscopic images of corresponding regions (FIG. 3C) showed that directed EVs bound to BT474, but not to MCF7 cells. Treatment with PBS generated no signal (not shown). Not all BT474 cells evidently bound to the EVs. This may be because not all of them express this ligand to the same extent; that HER2 receptor density varies in HER2-positive cells has been reported. Given that MCHB has an excellent bystander effect, not all tumor cells need to receive HChR6 mRNA, and thus the lack of binding of EVs to all the cells would not necessarily hamper effective therapy.

Figure 3D:
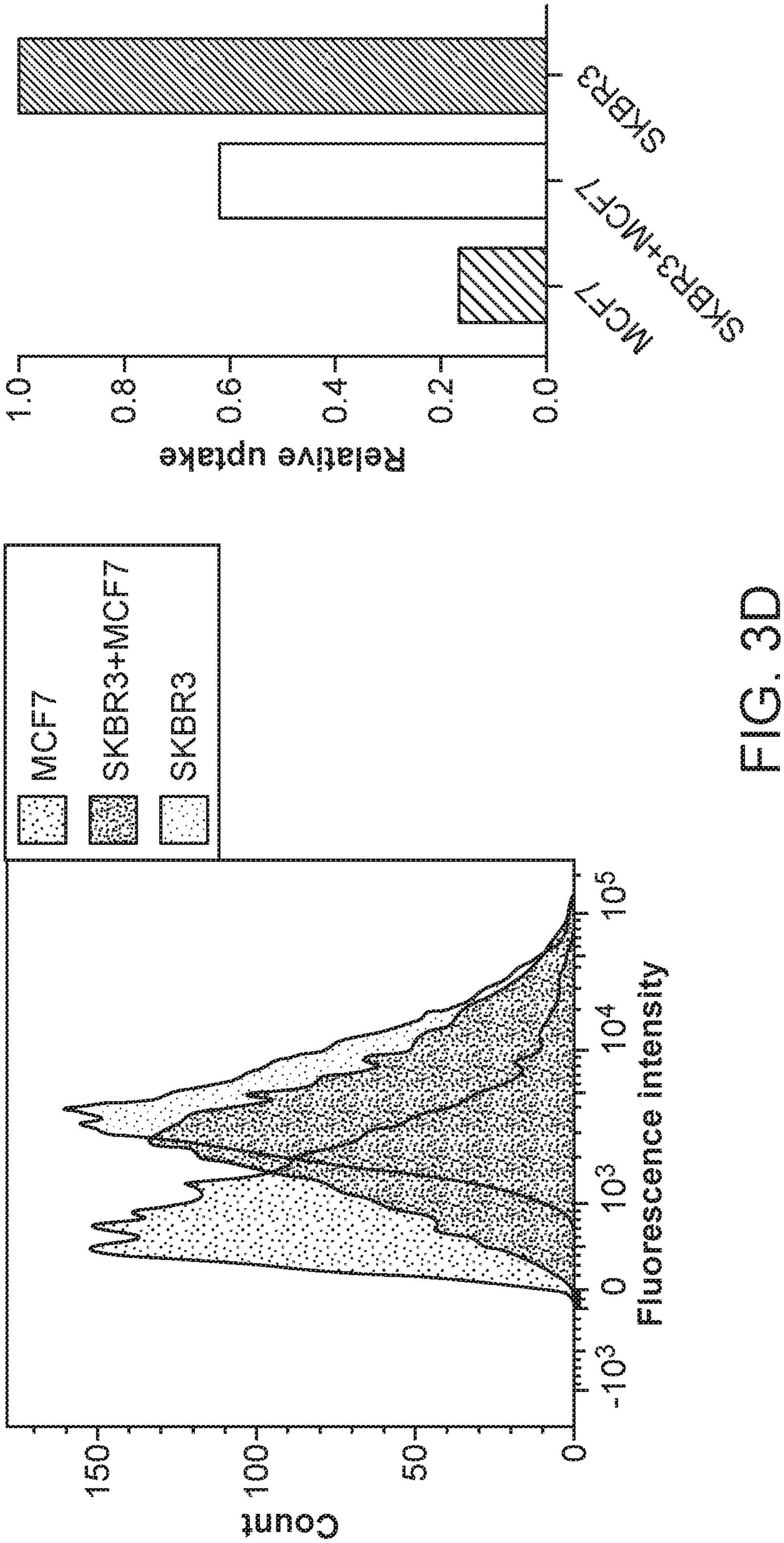

Flow cytometry was used to determine the binding of EVs to HER2-positive cells. As already mentioned, since BT474 cells tended to form clumps, the HER2-positive cells employed were SKBR3 (HER2 content, 913 ng/mg); these were treated with PKH26 dye-labeled directed EVs. Three-way binding comparisons were made: SKBR3 cells alone; MCF7 cells alone; or a 50:50 mixture of the two. the fluorescence intensity shift generated by SKBR3 cells was arbitrarily assigned a value of 1 (FIG. 3D). In contrast, MCF7 cells generated a shift of 0.17. Thus, the directed EVs exhibit a marked preference for binding to the HER2-positive cells. The shift exhibited by the mixture was 0.63, indicating that the concomitant presence of MCF7 cells did not interfere with the binding of directed EVs to SKRB3 cells, a beneficial outcome, as HER2-overexpressing tumors also contain HER2-negative cells.

Loading of EVs with mRNA, its EV-mediated delivery specifically to HER2-positive cells, and to implanted tumors in mice. Loading EVs with exogenous mRNA that remains functional has not been accomplished. Electroporation was attempted for this purpose. Non-electroporated EVs contained more mRNA than the electroporated (100-400V) ones, suggesting that the mRNA remained adhered to the surface of EVs, and was not internalized. The electroporation method succeeded in loading the EVs with GAPDH siRNA, indicating that this technique was sound (data not shown).

Figure 4A:
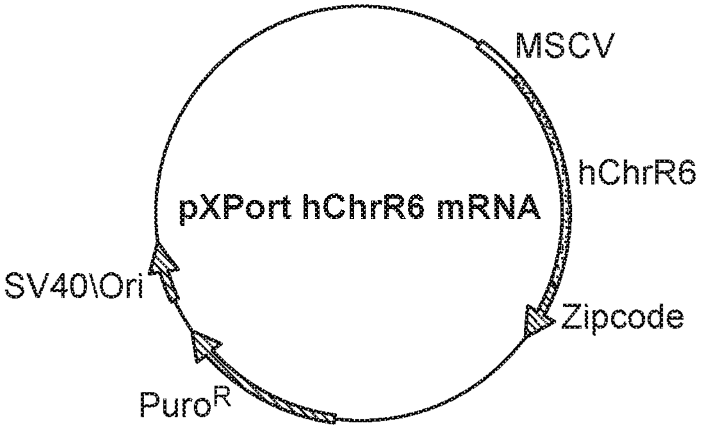
FIGS. 4A-4G.
Figure 4B:
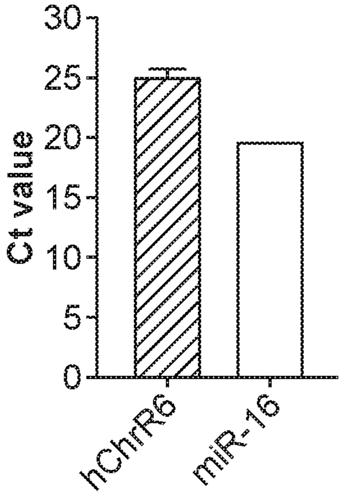
Figure 4C:
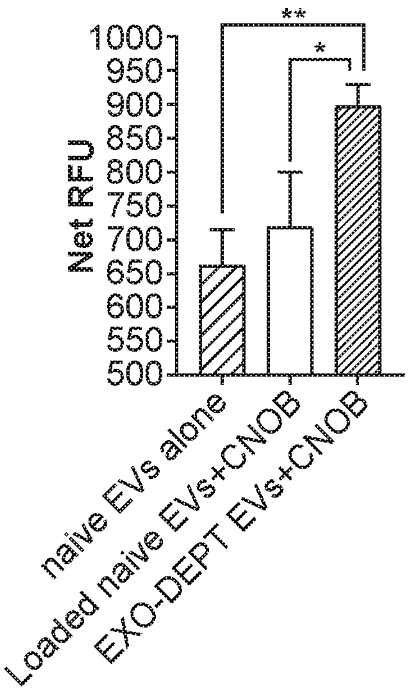
Figure 4D:
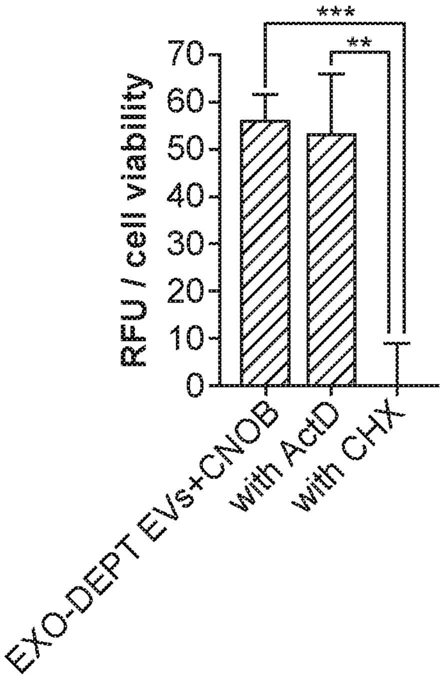

Presently described herein is a new method for inserting mRNA into the EVs. A special plasmid was constructed (FIG. 4A) using the "zipcode" technology and the SBI XPort plasmid. Two tandem copies of the EV-loading zipcode sequence ACCCTGCCGCCTGGACTCCGCCTGT-3') were inserted at the 3' UTR of the HchrR6 gene under the control of the constitutive MSCV promoter. This plasmid, named 'pXPort'hChrR6 mRNA', was used for transient transfection of 293FT cells. 4 days after transfection, the EVs were isolated from conditioned medium, the HChrR6 mRNA extracted and quantified: the Ct value is shown in FIG. 4B; it corresponds to 2 10-4 mRNA copy/EV.

The loaded EVs were incubated with EVHB (FIG. 3B), generating directed and loaded, (EXO-DEPT) EVs. These were tested for their ability to deliver HChrR6 mRNA to BT474 cells. The cells were incubated overnight with the EVs, or as control, with naïve but loaded, EVs (8 $10^8$/well). If the EVs succeeded in transmitting the HChrR6 mRNA, the recipient cells would acquire the capability to activate CNOB. This was assessed by determining MCHB generation (monitored by its fluorescence) following CNOB addition. EXO-DEPT EVs—but not the naïve-loaded EVs—enabled the recipient cells to convert CNOB into MCHB (FIG. 4C; $p<0.01$). Actinomycin D (transcriptional inhibitor) did not affect this, but cycloheximide (protein synthesis inhibitor) eliminated CNOB conversion by the cells ($p<0.001$). Thus, it was functional mRNA that was transferred by the EXO-DEPT EVs and for EVs to be able to do so they needed to be targeted to the HER2 receptor.

Figure 4E:
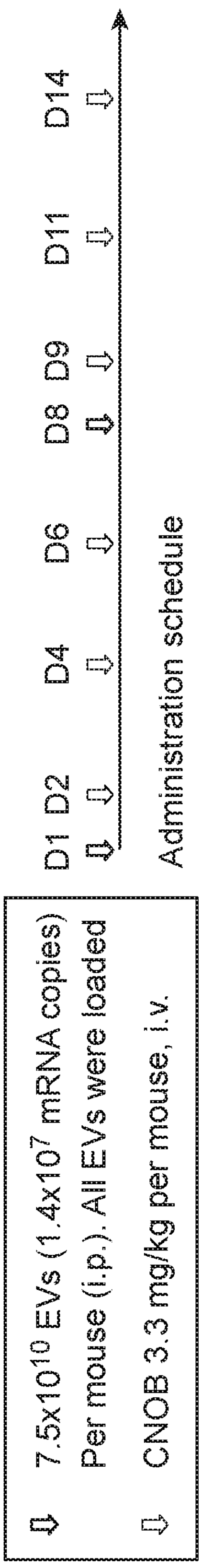

The effect of administration of EXO-DEPT EVs along with CNOB was tested on orthotopically implanted BT474 tumors in athymic mice; the treatment schedule (FIG. 4E) was guided by earlier PK/PD studies. The half-life of MCHB in plasma is 8.3 hours, indicating that administration of the regimen at 24-hour interval (or longer) would allow adequate clearance of the drug from plasma and avoid systemic toxicity. After measurable implanted tumors in mice were detected, they were randomly allocated into 5 treatment groups (n=6): untreated; loaded EVs only; CNOB only; undirected loaded EVs+CNOB; and EXO-DEPT-EVs+CNOB. The treatment was started with intraperitoneal injection of $2\times10^9$ EVs and, 24 hours later, of intravenous injection of CNOB (3.3 mg/kg in saline): corresponding controls received PBS (instead of EVs) or saline (instead of CNOB). Further doses (in the same amounts) were administered as shown in FIG. 4E.

Figure 4G:
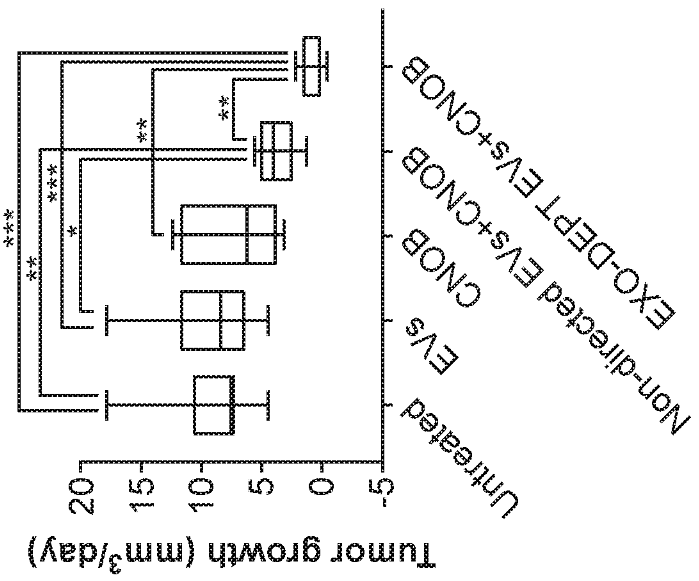
Figure 4F:
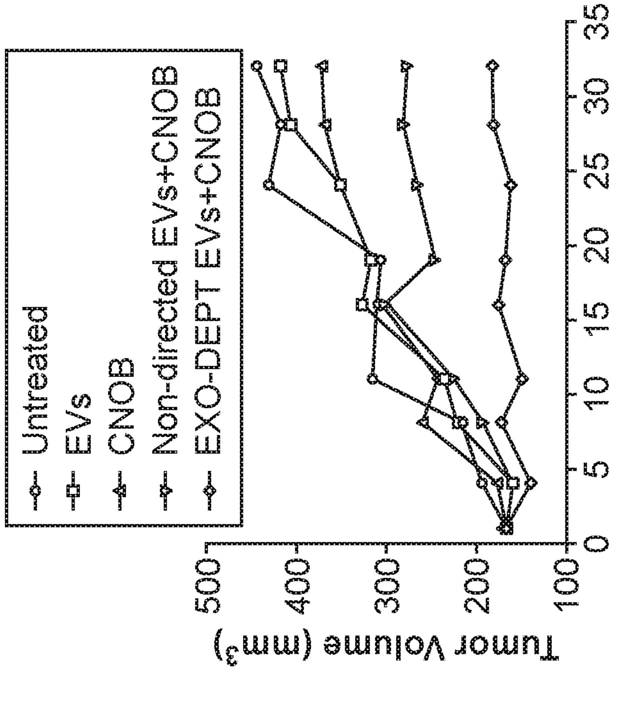

Tumor volume was recorded twice a week and each data point in FIG. 4F represents average value for a given treatment group. Slopes of linear regression, which represent tumor growth rate of individual mice, were calculated for each treatment group and are shown in Box and Whisker plot (FIG. 4G). Mice receiving EXO-DEPT EVs+CNOB treatment began to show statistically significant ($p<0.01$) difference in tumor volumes vs. the controls on day 11; this became more marked ($p<0.001$) as the experiment progressed (FIG. 4F). Note, that this group shows near-complete arrest of tumor growth. Tumor development was also mitigated in the loaded, undirected EVs+CNOB group, as was expected from the fact, referred to above, that EVs can extravasate through vessel fenestrations present in tumors; lack of effective lymphatic drainage in solid tumors further promotes this effect. That the EXO-DEPT EVs were twice as effective ($p<0.01$ compared to the non-directed EV groups) in suppressing tumor growth underscores the success of this targeting strategy. There was no significant difference among untreated, EV only, and CNOB only groups. A more detailed statistical analysis of these results is presented in Tables 1-4, presented hereinbelow. The experiment was stopped because the tumors in control groups had begun to exceed the volume allowed by the animal protocol. A prior experiment in which only two groups were used—EXO-DEPT plus CNOB-treated, and untreated control (n=5)—gave very similar results.

Discussion

EVs are receiving increasing attention as vehicles for safe delivery of drugs and exogenous biomolecules, such as silencing small RNAs, to tissues for therapeutic purposes. As directed delivery of such agents to specific tissues has obvious advantages, successful attempts have been made to fuse to EV surface, ligands that target specific receptors. Examples include delivery of doxorubicin by β-integrins-targeted EVs to tumors; use of epidermal growth factor receptor (EGFR)-targeted EVs to transport molecules, such as let-7 microRNA-7a (let7a), to breast cancer in mice; and cationized pullulan treated EVs to target asialoglycoprotein receptors specifically expressed by hepatocytes. Specific targeting of HER2 receptor by EVs decorated with EVHB represents further advance in this direction. ELISA analysis showed that for these EVs to bind the HER2 receptor, they needed to be directed, i.e. display EVHB; and both microscopic and flow cytometry approaches confirmed that the directed EVs bind selectively to HER2-positive cells.

A major advance reported here concerns the construction of EXO-DEPT EVs that not only specifically target the HER2 receptor but are also capable of delivering to them functional HChrR6 mRNA. Insertion of foreign mRNA into EVs has been a challenge. Electroporation has not succeeded. Utilization of a bacteriophage protein bridge between EVs and mRNA did result in successful loading; but this mRNA, when delivered by the EVs to recipient cells, was non-functional. These EXO-DEPT EVs, however, converted BT474 cells into CNOB activating entities, resulting in MCHB generation and cell killing. This effect was not inhibited by Actinomycin D, showing that the ingredient transferred by the EVs was indeed HChrR6 mRNA. EXO-DEPT EVs also effectively delivered the HChrR6 mRNA in vivo: when administered along with CNOB, they caused near-complete arrest of the growth of implanted orthotopic HER2-overexpressing breast cancer tumors in athymic mice. The presently described compositions and methods, for the first time, demonstrate the successful delivery of EV-mediated exogenous therapeutic mRNA to arrest growth of tumor cells.

While tumor growth was arrested, the tumors were not eliminated, and studies are in progress to further improve the EXO-DEPT/CNOB regimen. Measures under investigation include increased HChrR6 mRNA loading into the EVs, and dosage/regimen optimization of EXO-DEPT and CNOB. HChrR6 is also effective in activating another prodrug, CB1954, for which a safe dosage has been established in clinical trials. The effect of combined therapy with CNOB and CB1954 is also therefore being explored. In addition, immuno-competent mice are being used to combine EXO-DEPT/prodrug and immune-based antitumor effectors. As it is not known what effect the native content of EVs might have on recipient cells, it is preferable to minimize the EXU-DEPT EV dose needed for effective prodrug treatment. EVs can cross the blood brain barrier. Metastasis to the brain is a common complication of HER2-overexpressing breast cancer; thus, the EXU-DEPT/prodrug therapy may be useful and effective in treating, preventing or ameliorating such complications as metastasis of cancer to the brain.

The EVHB-based approach is generic. ML39 in EVHB can be replaced by other targeting ligands to make directed EVs for delivering desired biomolecules/drugs to any disease in which a marker is overexpressed. Examples of other receptors overexpressed in cancers are PSMA, bombasin, folate, transferrin, and sigma. This approach was also used to make dual function EVs, combining HER2-targeting capability with its visualization. In addition to ML39, such dual function EVs have been constructed to display one of the C1-C2-conjugated reporters: GLuc, mCherry, or eGFP. The possibility of adding additional functionality can further enhance the EV-based therapies. For example, the potential utility of EXU-DEPT EVs in treating brain metastasis are aided by combined display of ML39 along with the neural cell adhesion molecule (NCAM), which is expressed on the surface of neurons.

In conclusion, the EXO-DEPT/CNOB regimen is effective in specifically targeting and arresting tumor growth in vivo. Evidence indicates that such EVs can be generated from dendritic cells, using mRNA formulations instead of DNA-based plasmids, described in Example 2. Previous studies have demonstrated that patient-specific exosomes derived from dendritic cells can be reliably produced under GMP for clinical use. This favorably illustrates the EXO-DEPT approach for therapeutic development, and given its generic applicability, further warrants its evaluation in a broad range of clinical indications.

A video was recorded to show the predicted EVHB three-dimensional structure rotated 360 degrees at y-axis, followed by 360 degrees at x-axis. The ML39 scFv antibody consists of heavy and light chains: also included are a flexible linker for the desired protein orientation, a lactadherin leader sequence, and the lactadherin C1 and C2 domains.

Statistical Methods for in vivo Experiment. Five treatment groups are shown in Table 1, below:

TABLE 1

| Treatment | No. of Mice |
|---|---|
| untreated | 7 |
| EV | 6 |
| CNOB | 5 |
| EV + CNOB | 5 |
| EV/EVHB + CNOB | 6 |

These were ordered as listed, with 5 expected to be the most efficacious and 1 the least.

Each mouse was measured at nine time periods, days 0,3,7,11,16,19,24,28,32. A linear regression of tumor burden versus day was fit for each mouse, by ordinary least squares, and its slope calculated.

$s[i]$=slope of mouse[$i$]'s linear regression

The 29 s[i] values were used as comparison statistics for the 5 groups. [Reducing each mouse's data to a single summary statistic was done to avoid time series modeling assumptions.] The slopes were expected to be most positive in Group 1 and least positive in Group 5.

Table 2 shows the means, and standard errors (SE) for the slope statistics in the 5 groups, and also the endpoints of two-sided 95% student-t confidence intervals.

TABLE 2

| Group | 1 | 2 | 3 | 4 | 5 |
|---|---|---|---|---|---|
| Mean | 8.83 | 9.09 | 7.24 | 3.87 | 0.96 |
| SE | 1.57 | 1.8 | 1.8 | 0.73 | 0.36 |
| 5% | 4.99 | 4.46 | 2.25 | 1.84 | 0.03 |
| 95% | 12.68 | 13.72 | 12.24 | 5.89 | 1.88 |

The means decrease in the order predicted, Group 1 was the largest, Group 5 was the smallest. The 95% confidence interval for Group 5 lies below those for Groups 1-3, and just barely overlaps that for Group 4.

As shown in Table 3, two-sample two-sided t-tests were run comparing the Groups.

TABLE 3

| Compare | t-value | p-value |
|---|---|---|
| 5 vs 1: | −4.89 | .000 |
| 5 vs 2: | −4.43 | .001 |
| 5 vs 3: | −3.43 | .004 |
| 5 vs 4: | −3.58 | .003 |
| 4 vs 3: | −1.74 | .060 |
| 4 vs 2: | −2.69 | .012 |
| 4 vs 1: | −2.87 | .008 |
| 3 vs 2: | −0.72 | .240 |
| 3 vs 1: | −0.67 | .260 |
| 2 vs 1: | 0.11 | .540 |

Group 5 shows strong significance versus 1,2,3, and 4; Group 4 shows moderately strong significance versus 1 and 2, and borderline significance versus 3. There are no other significant comparisons.

The table above comprises 10 t-tests, raising the question of adjustment for multiple testing. To this end a permutation analysis was performed:

The 29 slope statistics were randomly reordered.

The reordered values were assigned to 5 groups, 7 in the first group, 6 in the second, etc.

The table of 10 t-values above was recomputed for the permuted data.

All of this was done 1000 times, from which a Null distribution of the largest absolute t-value among the 10 was obtained. The first line of Table 4, below, shows the upper percentile points for the largest of the 10:

TABLE 4

| Percentile | 90% | 95% | 97.5% | 99% |
|---|---|---|---|---|
| All 10: | 2.85 | 3.28 | 3.70 | 4.28 |
| 5 vs 1, 2, 3, 4: | 2.47 | 2.87 | 3.30 | 3.63 |
| 4 vs 1, 2, 3: | 2.40 | 2.81 | 3.15 | 3.50 |

The Group 5 comparisons, ranging in absolute value between 3.43 and 4.89, had all multiply-adjusted p-values less than 0.05 (i.e., above 3.28), and that 5 vs 1 and 5 vs 2 had $p<0.01$. [A computer-based version of Tukey's studentized range test was used.] The Tukey test is conservative in this case, because the expected order of the 5 treatments was stated before the analysis. The second line of the table concerns testing Group 5 versus all 4 other groups. Now the results for Group 5 are stronger, always attaining better than 0.025 multiple significance. The third line of the table relates to testing Group 4 versus 1,2, and 3. Group 4 attains significance 0.05 vs Group 1, nearly so vs Group 2, and not versus Group 3. Slopes of linear regression for each mouse, based on above analysis, are plated below.

Example 2

Figure 6:
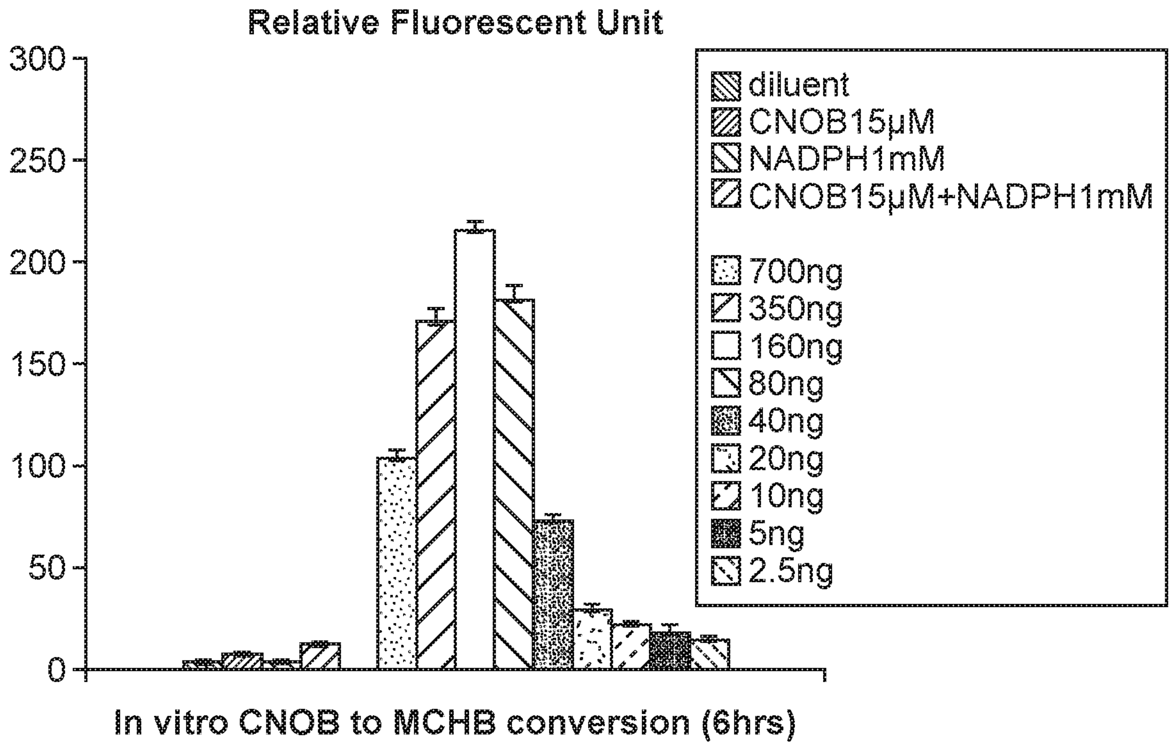
FIG. 6. Activity of HChrR6 synthesized from in vitro transcribed (IVT) mRNA.

Clinically safer loading of mRNA into the extracellular vesicles ("EVs" also called exosomes) provides stronger and longer-lasting expression in the recipient cells. This therapeutic regimen utilizes specific target EV-mediated delivery of mRNA into HER2-positive cancer cells (BT474). The mRNA encodes the enzyme (HChrR6) that activates prodrugs. Previously a plasmid was used to load the EVs (referred to from hereon as "plasmid EVs"). As these EVs are likely to contain the plasmid genetic material, their use in patients may introduce this genetic material. Therefore, as herein described for the first time, compositions and methods have been developed to generate EVs containing the mRNA without the use of plasmids, for targeted delivery of exosomes to the site of an extracellular receptor overexpressed in a disease, e.g., cancer. This method entails synthesis of the HChrR6 mRNA in vitro, using a standard kit (referred to from hereon as "IVT mRNA".

mRNA functionality. To test that this mRNA is functional, it was translated in vitro into the HChrR6 protein, again using a standard kit, and the activity of the resulting protein was assayed using a standard procedure (reaction mixture is given in FIG. 6). FIG. 6 shows that HChrR6 synthesized from the IVT mRNA is functional, and it converts CNOB into MCHB.

Figure 7:
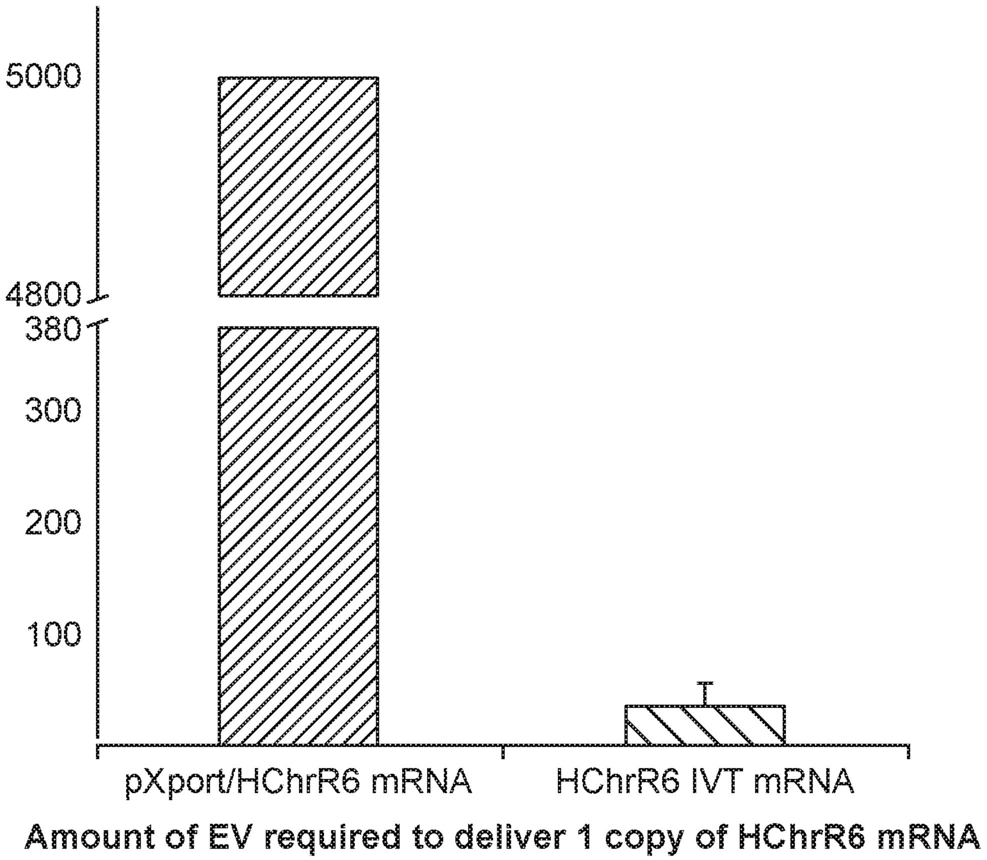
FIG. 7. Cells transfected with IVT HChrR6 mRNA generate EVs containing the mRNA FIG. 8. Cell mortality following delivery of IVT and plasmid EVs in the presence of CNOB.

IVT method generates EVs containing more mRNA. HEK293 cells transfected with this IVT HChrR6 mRNA generated EVs containing this mRNA. These are referred to herein as "IVT EVs". The IVT EVs contained much more mRNA than the plasmid EVs (qRT-PCR), such that while with the latter 5,000 EVs are needed to deliver one copy of the mRNA, with the former the same amount can be delivered with as few as 30-40 EVs (FIG. 7). These EVs were incubated with pure EVHB protein to generate IVT EXO-DEPTs.

Figure 8:
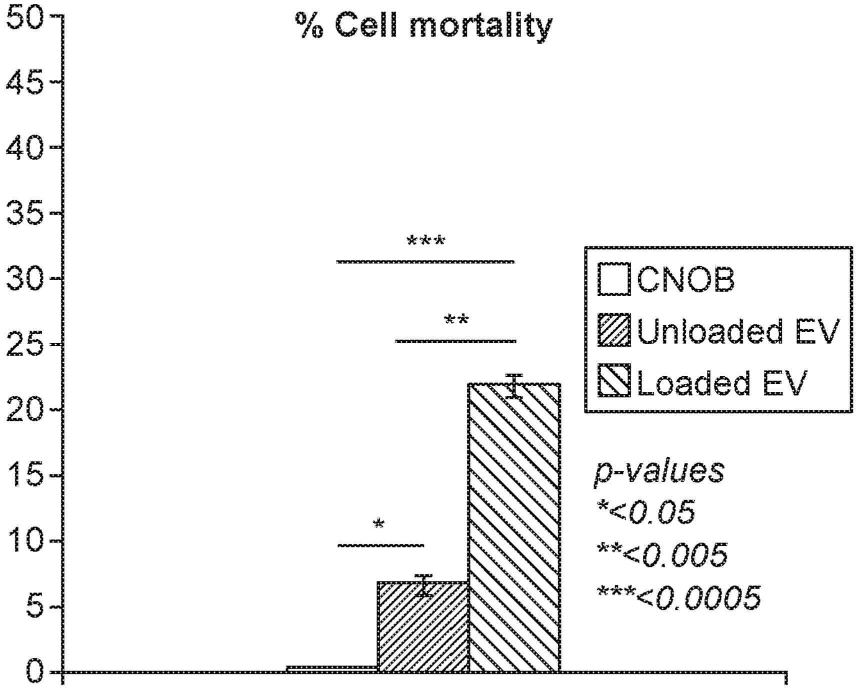
Figure 9:
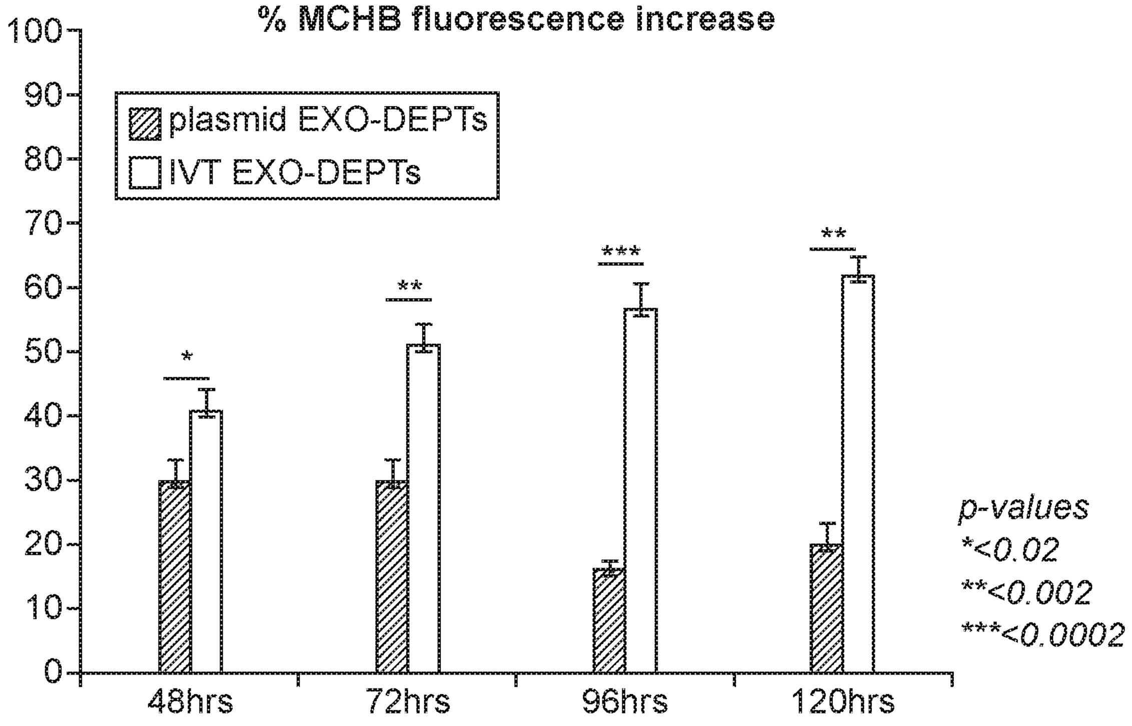
FIG. 9 illustrates recipient cells assayed for their capability to activate CNOB following delivery of IVT and plasmid EVs.

IVT EXO-DEPTs transfect BT474 cells, causing them to be killed by CNOB. This is shown in FIG. 8, indicating that the IVT mRNA remains functionally competent inside the recipient cells.

mRNA delivered to BT474 cells by the IVT EXO-DEPTs is more active and has longer duration of expression than that delivered by plasmid EXO-DEPTs. For this comparison, 10,000 mRNA copies were delivered, using $2.9\times10^5$ IVT EXO-DEPTs and $5\times10^7$ plasmid EXO-DEPTs, given that the former contain much more mRNA. The recipient BT474 cells were then assayed for their capability to activate CNOB at the different time points (up to 120 hours). The results are presented in FIG. 9. Three things may be noted: First, far fewer EVs were needed for the IVT EXO-DEPTs compared to plasmid EXO-DEPTs to deliver the same amount of mRNA; second, although the amount of mRNA introduced into the BT474 cells was the same by the two methods, the IVT EXO-DEPT-delivered mRNA is more active in converting CNOB into MCHB; and third, this capability lasts longer with the IVT EXO-DEPTs.

The significance of the stronger and longer-lasting expression of mRNA delivered by IVT EXO-DEPTs is that, in prodrug clinical trials involving gene delivery, the lack of sufficient amount of gene delivery and duration of expression have been found to be a cause for the lack of success of these trials. The compositions and methods provided herein represent a means to overcome such a problem.

Example 3

Use of CB1954

Figure 10:
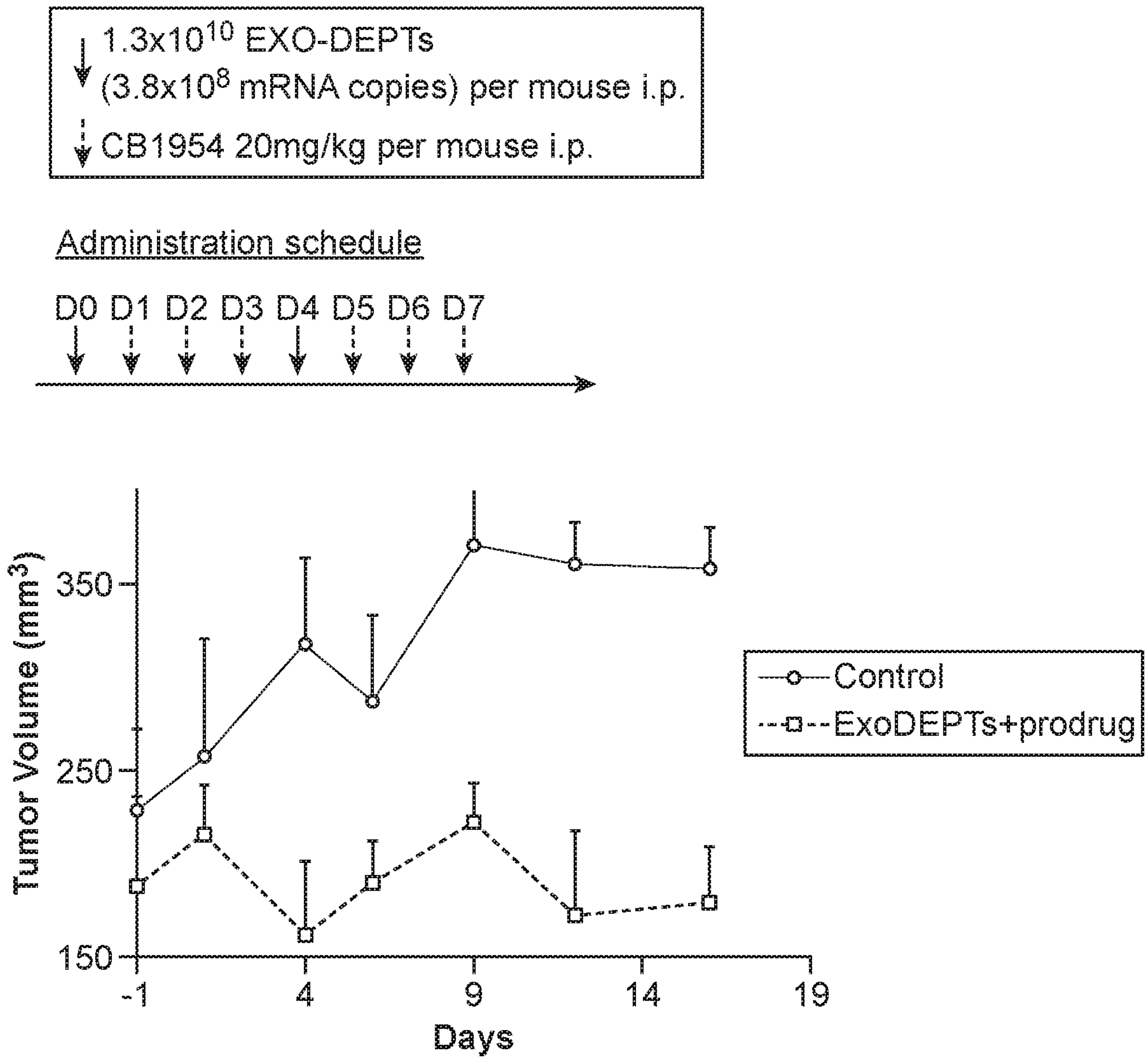
FIG. 10 shows early results in which IVT EXO-DEPTs in the presence of prodrug CB1954 were observed to suppress tumor growth in mice at a lower EV dose.

IVT EXO-DEPTs along with the prodrug CB1954 can suppress tumor growth in mice at a lower EV dose. The prodrug CB1954 (which HChrR6 can activate) is of great interest and is currently in clinical trials. BT474 tumors were orthotopically implanted in nu/nu mice as in Example 1. Both the EVs and CB1954 were injected intraperitoneally; the schedule based on PK considerations and the mRNA content of IVT EXO-DEPTs, as well as early results are shown in FIG. 10. The increased amount of mRNA in these EVs permitted the use of $1.3\times10^{10}$ per injection per mouse, much less than the $7.5\times10^{10}$ used for plasmid EXO-DEPTs.

Figure 11:
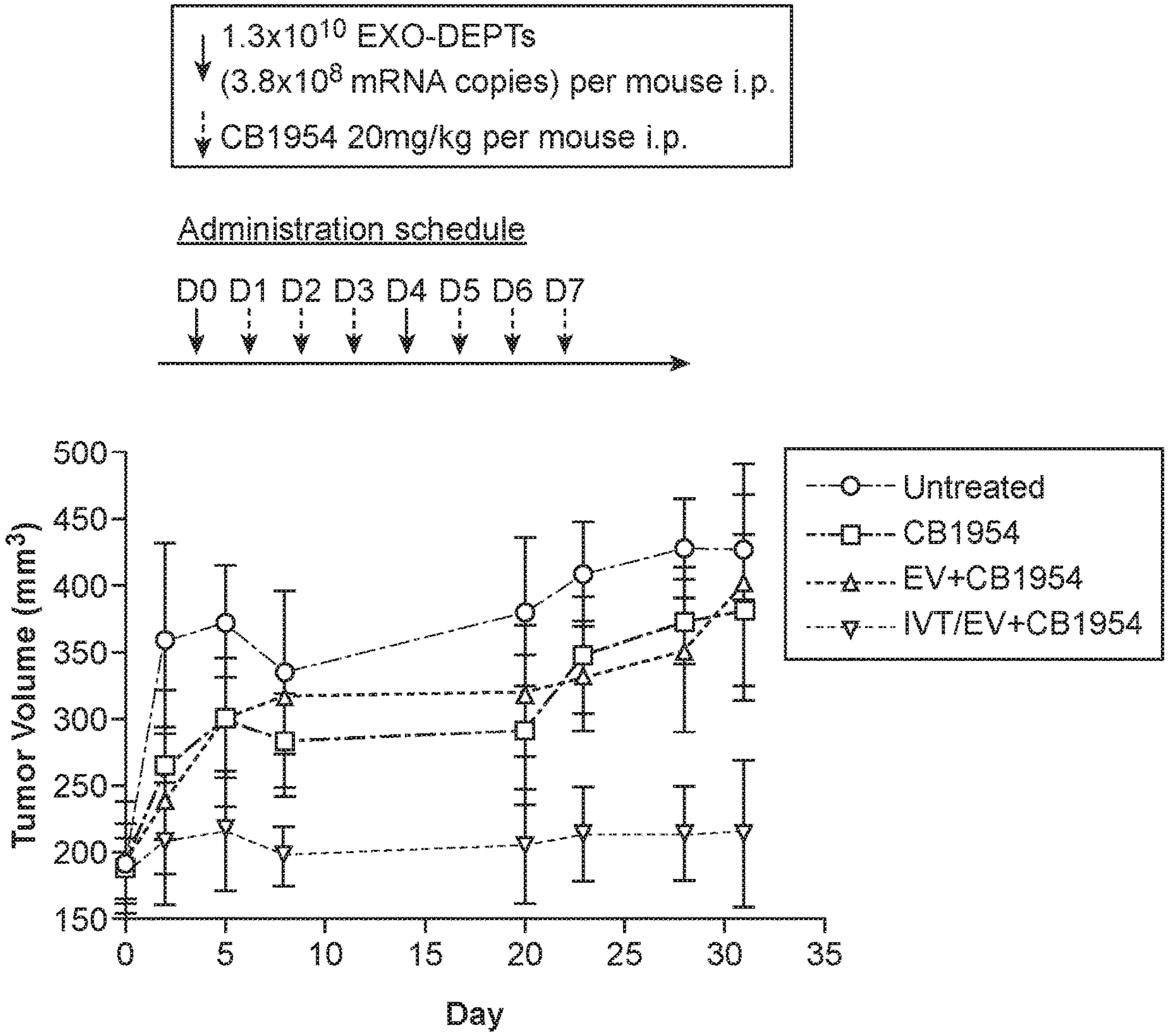
FIG. 11 provides additional evidence that IVT EXO-DEPTs with CB1954 almost completely arrested tumor growth, and had a p value is 0.0001 between the treated test and the control mice; this difference is highly significant.

Additional results are shown in FIG. 11, demonstrating that the IVT/EV+CB1954 therapeutic regimen nearly completely arrested tumor growth, with a high level of significance, while the untreated control showed vigorous growth.

The finding that CB1954 is effective with EXO-DEPT therapy makes clinical transfer easier. Furthermore, the fact that fewer EVs proved effective means that patients would require fewer injections.

REFERENCES

1. Padma V V. An overview of targeted cancer therapy. *Biomedicine* (Taipei) 2015, 5:19.
2. Williams E M, Little R F, Mowday A M et al. Nitroreductase gene-directed enzyme prodrug therapy: insights and advances toward clinical utility. *Biochem. J* 2015, 471:131-153.
3. Thorne S H, Barak Y, Liang W et al. CNOB/ChrR6, a new prodrug enzyme cancer chemotherapy. *Mol. Cancer Ther.* 2009, 8:333-341.
4. Barak Y, Ackerley D F, Dodge C J, et al. Analysis of novel soluble chromate and uranyl reductases and generation of an improved enzyme by directed evolution. *Appl. Environ. Microbiol.* 2006; 72:7074-7082.
5. Barak Y, Thome S H, Ackerley D F et al. New enzyme for reductive cancer chemotherapy, YieF, and its improvement by directed evolution. *Mol. Cancer Ther.* 2006; 5:97-103.
6. Eswaramoorthy S, Poulain S, Hienerwadel R et al. Crystal structure of ChrR—a quinone reductase with the capacity to reduce chromate. *PLoS One* 2012; 7:e36017.
7. Wang J H, Endsley A N, Green C E, Matin A C. Utilizing native fluorescence imaging, modeling and simulation to examine pharmacokinetics and therapeutic regimen of a novel anticancer prodrug. *BMC Cancer* 2016; 16:524.
8. Lelekakis M. Moseley J M, Martin T J et al. A novel orthotopic model of breast cancer metastasis to bone. *Clin. Exp. Metastasis* 1999; 17:163-170.
9. Franklin M C, Carey K D, Vajdos F F et al. Insights into ErbB signaling from the structure of the ErbB2-pertuzumab complex. *Cancer Cell* 2004; 5:317-328.
10. Yarden Y, Sliwkowski M X. Untangling the ErbB signalling network. *Nat. Rev Mol. Cell. Biol.* 2001; 2:127-137.
11. Slamon D J, Clark G M, Wong S G et al. Human breast cancer: correlation of relapse and survival with amplification of the HER-2/neu oncogene. *Science* 1987; 235: 177-182.
12. Slamon D J, Godolphin W, Jones L A et al. Studies of the HER-2/neu proto-oncogene in human breast and ovarian cancer. *Science* 1989; 244:707-712.
13. Slamon D, Eiermann W, Robert N et al. Adjuvant trastuzumab in HER2-positive breast cancer. *N Engl. J. Med.* 2011; 365:1273-1283.
14. Romond E H, Perez E A, Bryant J et al. Trastuzumab plus adjuvant chemotherapy for operable HER2-positive breast cancer. *N Med.* 2005; 353:1673-1684.

15. Pegram M, Hsu 5, Lewis G et al. Inhibitory effects of combinations of HER-2/neu antibody and chemotherapeutic agents used for treatment of human breast cancers. *Oncogene* 1999; 18:2241-2251.
16. Konecny G E, Pegram M D, Venkatesan N et al. Activity of the dual kinase inhibitor lapatinib (GW572016) against HER-2-overexpressing and trastuzumab-treated breast cancer cells. *Cancer Res.* 2006; 66:1630-1639.
17. Geyer C E, Forster J, Lindquist D et al. Lapatinib plus capecitabine for HER2-positive advanced breast cancer. *N Engl. J. Med.* 2006; 355:2733-2743.
18. Duarte S, Carle G, Faneca. H et al. Suicide gene therapy in cancer: where do we stand now? *Cancer Lett.* 2012; 324:160-170.
19. Bai L, Shao H, Wang H et al. Effects of Mesenchymal Stem Cell-Derived Exosomes on Experimental Autoimmune Uveitis. *Sci. Rep.* 2017; 7:4323.
20. Colombo M, Raposo G, Thery C. Biogenesis, secretion, and intercellular interactions of exosomes and other extracellular vesicles. *Annu. Rev. Cell. Dev. Biol.* 2014; 30: 255-289.
21. Delcayre A, Estelles A, Sperinde J et al. Exosome Display technology: applications to the development of new diagnostics and therapeutics. *Blood Cells Mol. Dis.* 2005; 35:158-168.
22. El Andaloussi S, Lakhal S, Mager I, Wood M J. Exosomes for targeted siRNA delivery across biological barriers. *Adv. Drug Deliv. Rev.* 2012.
23. Ha D, Yang N, Nadithe V. Exosomes as therapeutic drug carriers and delivery vehicles across biological membranes: current perspectives and future challenges. *Acta Pharm. Sin. B.* 2016; 6:287-296.
24. van den Boom J G, Dassler J, Coch C et al. Exosomes as nucleic acid nanocarriers. *Adv. Drug Deliv. Rev.* 2012.
25. van den Boom J G, Schlee M, Coch C, Hartmann G. SiRNA delivery with exosome nanoparticles. *Nat. Biotechnol.* 29:325-326.
26. Rainov N G. A phase III clinical evaluation of herpes simplex virus type 1 thymidine kinase and ganciclovir gene therapy as an adjuvant to surgical resection and radiation in adults with previously untreated glioblastoma multiforme. *Hum. Gene Ther.* 2000; 11:2389-2401.
27. Schenk E, Essand M, Bangma C H et al. Clinical adenoviral gene therapy for prostate cancer. *Hum. Gene Ther.* 2010; 21:807-813.
28. Onion D, Patel P, Pineda R G et al. Antivector and tumor immune responses following adenovirus-directed enzyme prodrug therapy for the treatment of prostate cancer. *Hum. Gene Ther.* 2009; 20:1249-1258.
29. Patel P, Young J G, Mautner V et al. A phase I/II clinical trial in localized prostate cancer of an adenovirus expressing nitroreductase with CB1954 [correction of CB1984]. *Mol. Ther.* 2009; 17:1292-1299.
30. Zabner J, Fasbender A J, Moninger T et al. Cellular and molecular barriers to gene transfer by a cationic lipid. *J Biol. Chem.* 1995; 270:18997-19007.
31. Zou S, Scarff K, Nantz M H, Hecker J G. Lipid-mediated delivery of RNA is more efficient than delivery of DNA in non-dividing cells. *Int. J. Pharm.* 389:232-243.
32. Okumura K, Nakase M, Inui M et al. Bax mRNA therapy using cationic liposomes for human malignant melanoma. *The journal of gene medicine* 2008; 10:910-917.
33. Li X, Stuckert P, Bosch I et al. Single-chain antibody-mediated gene delivery into ErbB2-positive human breast cancer cells. *Cancer Gene Ther.* 2001; 8:555-565.
34. Kanada M, Bachmann M H, Hardy J W et al. Differential fates of biomolecules delivered to target cells via extracellular vesicles. *Proc. Natl. Acad. Sci. U S. A.* 2015; 112:E1433-1442.
35. Kelley L A, Mezulis S, Yates C M et al. The Phyre2 web portal for protein modeling, prediction and analysis. *Nat. Protoc.* 2015; 10: 845-858.
36. Alvarez-Erviti L, Scow Y, Yin H et al. Delivery of siRNA to the mouse brain by systemic injection of targeted exosomes. *Nat. Biotechnol.* 2011; 29:341-345.
37. Charan J, Kantharia N D. How to calculate sample size in animal studies? *J. Pharmacol. Pharmacother.* 2013; 4:303-306.
38. Otzen D E, Blans K, Wang H et al. Lactadherin binds to phosphatidylserine-containing vesicles in a two-step mechanism sensitive to vesicle size and composition. *Biochim. Biophys. Acta* 2012; 1818:1019-1027.
39. Hendriks B S, Klinz S G, Reynolds J G et al. Impact of tumor HER2/ERBB2 expression level on HER2-targeted liposomal doxorubicin-mediated drug delivery: multiple low-affinity interactions lead to a threshold effect. *Mol. Cancer Ther.* 2013; 12:1816-1828.
40. Hung M E, Leonard J N. A platform for actively loading cargo RNA to elucidate limiting steps in E V-mediated delivery. J Extracell Vesicles 2016; 5:31027.
41. Momen-Heravi F, Bala S, Bukong T, Szabo G. Exosome-mediated delivery of functionally active miRNA-155 inhibitor to macrophages. *Nanomedicine* 2014; 10:1517-1527.
42. Bolukbasi M F, Mizrak A, Ozdener G B et al. miR-1289 and "Zipcode"-like Sequence Enrich mRNAs in Microvesicles. *Mol. Ther. Nucleic Acids* 2012; 1:e10.
43. Tian Y, Li S, Song J et al. A doxombicin delivery platform using engineered natural membrane vesicle exosomes for targeted tumor therapy. *Biomaterials* 2014; 35:2383-2390.
44. Kooijmans S A, Aleza C G, Roffler S R et al. Display of GPI-anchored anti-EGFR nanobodies on extracellular vesicles promotes tumour cell targeting. *J. Extracell. Vesicles* 2016; 5:31053.
45. Ohno 5, Takanashi M, Sudo K et al. Systemically injected exosomes targeted to EGFR deliver antitumor microRNA to breast cancer cells. *Mol. Ther.* 2013; 21:185-191.
46. Tamura R, Uemoto S, Tabata Y. Augmented liver targeting of exosomes by surface modification with cationized pullulan. *Acta Biomater.* 2017; 57:274-284.
47. Chung-Faye G, Palmer D, Anderson D et al. Virus-directed, enzyme prodrug therapy with nitroimidazole reductase: a phase I and pharmacokinetic study of its prodrug, CB1954. *Chit Cancer Res.* 2001; 7:2662-2668.
48. Fruhbeis C, Frohlich D, Kramer-Albers E M. Emerging roles of exosomes in neuron-glia communication. *Front Physiol.* 2012; 3:119.
49. Kalani A, Tyagi A, Tyagi N. Exosomes: mediators of neurodegeneration, neuroprotection and therapeutics. *Mol. Neurobiol.* 2014; 49:590-600.
50. Xin H, Li Y, Chopp M. Exosomes/miRNAs as mediating cell-based therapy of stroke. *Front Cell Neurosci.* 2014; 8:377.
51. Yang T Z, Martin P, Fogarty B et al. Exosome Delivered Anticancer Drugs Across the Blood-Brain Barrier for Brain Cancer Therapy in Danio Rerio. *Pharmaceutical Research* 2015; 32:2003-2014.
52. Stemmler H J, Schmitt M, Willems A et al. Ratio of trastuzumab levels in serum and cerebrospinal fluid is altered in HER2-positive breast cancer patients with brain metastases and impairment of blood-brain barrier. *Anticancer Drugs* 2007; 18:23-28.
53. Reynolds A R, Moein Moghimi S, Hodivala-Dilke K. Nanoparticle-mediated gene delivery to tumour neovasculature. *Trends Mol. Med.* 2003; 9:2-4.
54. Lu Y, Low P S. Immunotherapy of folate receptor-expressing tumors: review of recent advances and future prospects. *J. Control Release* 2003; 91:17-29.
55. Kasperzyk J L, Finn S P, Flavin R et al. Prostate-specific membrane antigen protein expression in tumor tissue and risk of lethal prostate cancer. *Cancer Epidemiol. Biomarkers Prev.* 2013; 22:2354-2363.
56. Akhtar M J, Ahamed M, Alhadlaq H A et al. Targeted anticancer therapy: overexpressed receptors and nanotechnology. *Clip. Chirp. Acta.* 2014; 436:78-92.
57. Jensen M, Berthold F. Targeting the neural cell adhesion molecule in cancer. Cancer Lett. 2007; 258:9-21.
58. Amin A, Dudek A Z, Logan I F et al. Survival with AGS-003, an autologous dendritic cell-based immunotherapy, in combination with sunitinib in unfavorable risk patients with advanced renal cell carcinoma (RCC): Phase 2 study results. *J. Immunother. Cancer.* 2015; 3:14.
59. Figlin R A, Amin A, Dudek A et al. Phase II study combining personalized dendritic cell (DC)-based therapy, AGS-003, with sunitinib in metastatic renal cell carcinoma (mRCC). *J. Clin. Oncol.* 2012; 30:348.
60. Jurisica I, Gamble A H, Tcherepanova I Y et al. Identification of multifunctional cytotoxic T-cell subsets as immune correlates with clinical outcomes in a phase II study of AGS-003, an autologous dendritic cell-based therapy administered to patients with newly diagnosed, metastatic RCC. *J. Clin. Oncol.* 2012; 30:80.
61. Nicolette C A, Healey D, Tcherepanova I et al. Dendritic cells for active immunotherapy: optimizing design and manufacture in order to develop commercially and clinically viable products. *Vaccine* 2007; 25 Suppl. 2:B47-60.

The preceding merely illustrates the principles used in the present disclosure. It will be appreciated that those skilled in the art will be able to devise various arrangements which, although not explicitly described or shown herein, embody the principles of the present disclosure and are included within its spirit and scope. Furthermore, all examples and conditional language recited herein are principally intended to aid the reader in understanding the principles of the disclosure and the concepts contributed by the inventors to furthering the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

What is claimed is:

1. A composition comprising an extracellular-receptor-targeted exosome presenting a targeting moiety on its surface, wherein the exosome comprises:

(a) a chimeric protein comprising:

i) a lactadherin leader sequence (LS) for migration to the exosome surface, ii) a targeting moiety having high affinity for an extracellular receptor overexpressed in a disease, iii) a lactadherin C1-C2 domain, and iv) an epitope tag for purification; and (b) an active agent included in the exosome, wherein the active agent is a functional mRNA encoding ChrR.

2. The composition of claim 1, wherein ChrR converts a prodrug to a drug, and wherein the prodrug is selected from the group consisting of: 6-chloro-9-nitro-5-oxo-5H-benzo-(a)-phenoxazine (CNOB); 2,5-diaziridinyl-3-(hydroxymethyl)-6-methyl-1,4-benzoquinone; 5-aziridinyl-2,4-dinitrobenzamide (CB 1954); 1,4-bis[[2-(dimethylamino) ethyl] amino]-5,8-dihydroxyanthracene-9,10-dione (AQ4); SN 23862; SN 27217; mitomycin C; 17-allylamino-17-demethoxygeldanamycin (17-AAG); and combinations thereof.

3. The composition of claim 1, wherein the targeting moiety is an antibody or functional fragment thereof (e.g., scFv).

4. The composition of claim 1, wherein the targeting moiety is an extracellular receptor targeting scFv antibody.

5. A method of treating or ameliorating a disease or disorder in which an extracellular receptor is overexpressed, comprising administering to a subject in need thereof a composition comprising the extracellular receptor-targeted exosome of claim 1.

6. The method of claim 5, wherein the disease is cancer.

7. A method of producing an extracellular-receptor-targeted exosome, said method comprising:

transfecting eukaryotic cells with an expression construct that expresses the chimeric protein of claim 1;

isolating exosomes; and loading an active agent into the exosome.

8. The method of claim 5, wherein ChrR converts a prodrug to a drug, and wherein the prodrug is selected from the group consisting of: 6-chloro-9-nitro-5-oxo-5H-benzo-(a)-phenoxazine (CNOB); 2,5-diaziridinyl-3-(hydroxymethyl)-6-methyl-1,4-benzoquinone; 5-aziridinyl-2,4-dinitrobenzamide (CB 1954); 1,4-bis[[2-(dimethylamino) ethyl] amino]-5,8-dihydroxyanthracene-9,10-dione (AQ4); SN 23862; SN 27217; mitomycin C; 17-allylamino-17-demethoxygeldanamycin (17-AAG); and combinations thereof.

9. The method of claim 7, wherein the targeting moiety in the chimeric protein is an extracellular receptor-targeting antibody or functional fragment thereof (e.g., scFv).

10. The composition of claim 1, wherein the targeting moiety is an antibody that specifically binds to HER2.

11. The composition of claim 1, wherein the chimeric protein (a) comprises the amino acid sequence of SEQ ID NO:2.

12. The composition of claim 1, wherein the mRNA encoding ChrR comprises the nucleotide sequence of SEQ ID NO:1.

* * * * *

SEQUENCE LISTING

```
<160> NUMBER OF SEQ ID NOS: 2

<210> SEQ ID NO 1
<211> LENGTH: 188
<212> TYPE: PRT
<213> ORGANISM: E. coli

<400> SEQUENCE: 1

Met Ser Glu Lys Leu Gln Val Val Thr Leu Leu Gly Ser Leu Arg Lys
1               5                   10                  15

Gly Ser Phe Asn Gly Met Val Ala Arg Thr Leu Pro Lys Ile Ala Pro
            20                  25                  30

Ala Ser Met Glu Val Asn Ala Leu Pro Ser Ile Ala Asp Ile Pro Leu
        35                  40                  45

Tyr Asp Ala Asp Val Gln Gln Glu Asp Gly Phe Pro Ala Thr Val Glu
    50                  55                  60

Ala Leu Ala Glu Gln Ile Arg Gln Ala Asp Gly Val Val Ile Val Thr
65                  70                  75                  80

Pro Glu Tyr Asn Tyr Ser Val Pro Gly Gly Leu Lys Asn Ala Ile Asp
                85                  90                  95

Trp Leu Ser Arg Leu Pro Asp Gln Pro Leu Ala Gly Lys Pro Val Leu
            100                 105                 110

Ile Gln Thr Ser Ser Met Gly Val Ile Gly Gly Ala Arg Cys Gln Tyr
        115                 120                 125

His Leu Arg Gln Ile Leu Val Phe Leu Asp Ala Met Val Met Asn Lys
    130                 135                 140

Pro Glu Phe Met Gly Gly Val Ile Gln Asn Lys Val Asp Pro Gln Thr
145                 150                 155                 160

Gly Glu Val Ile Asp Gln Ser Thr Leu Asp His Leu Thr Gly Gln Leu
```

```
                165                 170                 175

Thr Ala Phe Gly Glu Phe Ile Gln Arg Val Lys Ile
            180                 185


<210> SEQ ID NO 2
<211> LENGTH: 621
<212> TYPE: PRT
<213> ORGANISM: Artificial sequence
<220> FEATURE:
<223> OTHER INFORMATION: synthetic sequence

<400> SEQUENCE: 2

Met Gln Val Ser Arg Val Leu Ala Ala Leu Cys Gly Met Leu Leu Cys
1               5                   10                  15

Ala Ser Gly Leu Phe Ala Ala Ser Gly Gln Val Gln Leu Val Gln Ser
            20                  25                  30

Gly Ala Glu Val Lys Lys Pro Gly Glu Ser Leu Lys Ile Ser Cys Lys
        35                  40                  45

Gly Ser Gly Tyr Ser Phe Thr Ser Tyr Trp Ile Ala Trp Val Arg Gln
    50                  55                  60

Met Pro Gly Lys Gly Leu Glu Tyr Met Gly Leu Ile Tyr Pro Gly Asp
65                  70                  75                  80

Ser Asp Thr Lys Tyr Ser Pro Ser Phe Gln Gly Gln Val Thr Ile Ser
                85                  90                  95

Val Asp Lys Ser Val Ser Thr Ala Tyr Leu Gln Trp Ser Ser Leu Lys
            100                 105                 110

Pro Ser Asp Ser Ala Val Tyr Phe Cys Ala Arg His Asp Val Gly Tyr
        115                 120                 125

Cys Ser Ser Ser Asn Cys Ala Lys Trp Pro Glu Tyr Phe Gln His Trp
    130                 135                 140

Gly Gln Gly Thr Leu Val Thr Val Ser Ser Gly Gly Gly Ser Gly Gly
145                 150                 155                 160

Gly Gly Ser Gly Gly Gly Gly Ser Gln Ser Val Leu Thr Gln Pro Pro
                165                 170                 175

Ser Val Ser Ala Ala Pro Gly Gln Lys Val Thr Ile Ser Cys Ser Gly
            180                 185                 190

Ser Ser Ser Asn Ile Gly Asn Asn Tyr Val Ser Trp Tyr Gln Gln Leu
        195                 200                 205

Pro Gly Thr Ala Pro Lys Leu Leu Ile Tyr Asp His Thr Asn Arg Pro
    210                 215                 220

Ala Gly Val Pro Asp Arg Phe Ser Gly Ser Lys Ser Gly Thr Ser Ala
225                 230                 235                 240

Ser Leu Ala Ile Ser Gly Phe Arg Ser Glu Asp Glu Ala Asp Tyr Tyr
                245                 250                 255

Cys Ala Ser Trp Asp Tyr Thr Leu Ser Gly Trp Val Phe Gly Gly Gly
            260                 265                 270

Thr Lys Leu Thr Val Leu Gly Gly Gly Gly Ser Gly Gly Gly Thr Glu
        275                 280                 285

Tyr Ile Cys Gln Cys Pro Val Gly Tyr Ser Gly Ile His Cys Glu Thr
    290                 295                 300

Gly Cys Ser Thr Gln Leu Gly Met Glu Gly Gly Ala Ile Ala Asp Ser
305                 310                 315                 320

Gln Ile Ser Ala Ser Ser Val Tyr Met Gly Phe Met Gly Leu Gln Arg
                325                 330                 335

Trp Gly Pro Glu Leu Ala Arg Leu Tyr Arg Thr Gly Ile Val Asn Ala
```

-continued

```
            340                 345                 350

Trp Thr Ala Ser Asn Tyr Asp Ser Lys Pro Trp Ile Gln Val Asn Leu
        355                 360                 365

Leu Arg Lys Met Arg Val Ser Gly Val Met Thr Gln Gly Ala Ser Arg
    370                 375                 380

Ala Gly Arg Ala Glu Tyr Leu Lys Thr Phe Lys Val Ala Tyr Ser Leu
385                 390                 395                 400

Asp Gly Arg Lys Phe Glu Phe Ile Gln Asp Glu Ser Gly Gly Asp Lys
                405                 410                 415

Glu Phe Leu Gly Asn Leu Asp Asn Asn Ser Leu Lys Val Asn Met Phe
            420                 425                 430

Asn Pro Thr Leu Glu Ala Gln Tyr Ile Arg Leu Tyr Pro Val Ser Cys
        435                 440                 445

His Arg Gly Cys Thr Leu Arg Phe Glu Leu Leu Gly Cys Glu Leu His
    450                 455                 460

Gly Cys Ser Glu Pro Leu Gly Leu Lys Asn Asn Thr Ile Pro Asp Ser
465                 470                 475                 480

Gln Met Ser Ala Ser Ser Ser Tyr Lys Thr Trp Asn Leu Arg Ala Phe
                485                 490                 495

Gly Trp Tyr Pro His Leu Gly Arg Leu Asp Asn Gln Gly Lys Ile Asn
            500                 505                 510

Ala Trp Thr Ala Gln Ser Asn Ser Ala Lys Glu Trp Leu Gln Val Asp
        515                 520                 525

Leu Gly Thr Gln Arg Gln Val Thr Gly Ile Ile Thr Gln Gly Ala Arg
    530                 535                 540

Asp Phe Gly His Ile Gln Tyr Val Ala Ser Tyr Lys Val Ala His Ser
545                 550                 555                 560

Asp Asp Gly Val Gln Trp Thr Val Tyr Glu Glu Gln Gly Ser Ser Lys
                565                 570                 575

Val Phe Gln Gly Asn Leu Asp Asn Asn Ser His Lys Lys Asn Ile Phe
            580                 585                 590

Glu Lys Pro Phe Met Ala Arg Tyr Val Arg Val Leu Pro Val Ser Trp
        595                 600                 605

His Asn Arg Ile Thr Leu Arg Leu Glu Leu Leu Gly Cys
    610                 615                 620
```